US009695278B2

(12) United States Patent
Kagumba et al.

(10) Patent No.: US 9,695,278 B2
(45) Date of Patent: Jul. 4, 2017

(54) POLYESTER CO-PHOSPHONATES

(71) Applicant: FRX Polymers, Inc., Chelmsford, MA (US)

(72) Inventors: Lawino Kagumba, Cambridge, MA (US); Marc-Andre Lebel, Boxborough, MA (US); Jan-Pleun Lens, Boston, MA (US); Youmi Jeong, Boxborough, MA (US)

(73) Assignee: FRX POLYMERS, INC., Chelmsford, MA (US)

( * ) Notice: Subject to any disclaimer, the term of this patent is extended or adjusted under 35 U.S.C. 154(b) by 56 days.

(21) Appl. No.: 13/932,270

(22) Filed: Jul. 1, 2013

(65) Prior Publication Data
US 2014/0000751 A1 Jan. 2, 2014

Related U.S. Application Data

(60) Provisional application No. 61/666,005, filed on Jun. 29, 2012.

(51) Int. Cl.
*C08G 63/692* (2006.01)
*C08G 63/91* (2006.01)
*C08L 67/02* (2006.01)
*D03D 15/00* (2006.01)
*C08G 79/04* (2006.01)

(52) U.S. Cl.
CPC ....... *C08G 63/916* (2013.01); *C08G 63/6926* (2013.01); *C08L 67/02* (2013.01); *D03D 15/00* (2013.01); *D10B 2331/04* (2013.01)

(58) Field of Classification Search
CPC .............. C08G 63/692–63/6928; C08G 79/04
See application file for complete search history.

(56) References Cited

U.S. PATENT DOCUMENTS

| | | | | |
|---|---|---|---|---|
| 3,056,761 A | * | 10/1962 | Luckert et al. | 528/194 |
| 3,412,070 A | * | 11/1968 | Jakob et al. | 528/287 |
| 3,489,722 A | * | 1/1970 | Shinta et al. | 528/278 |
| 3,719,727 A | | 3/1973 | Masai et al. | |
| 3,928,283 A | * | 12/1975 | Masai et al. | C07F 9/4021 260/DIG. 24 |
| 4,328,174 A | * | 5/1982 | Schmidt et al. | 528/167 |
| 4,719,279 A | * | 1/1988 | Kauth | C08G 63/6926 525/462 |
| 4,782,123 A | * | 11/1988 | Kauth et al. | 525/437 |
| 5,298,591 A | * | 3/1994 | Choe | 528/190 |
| 6,055,711 A | * | 5/2000 | Weil et al. | 28/151 |
| 6,153,212 A | * | 11/2000 | Mao | A61K 9/1647 424/426 |
| 6,265,533 B1 | * | 7/2001 | Regel et al. | 528/487 |
| 6,861,499 B2 | | 3/2005 | Vinciguerra et al. | |
| 7,645,850 B2 | * | 1/2010 | Freitag | 528/196 |
| 7,816,486 B2 | | 10/2010 | Freitag et al. | |
| 8,389,664 B2 | | 3/2013 | Freitag et al. | |
| 2005/0245647 A1 | | 11/2005 | Masuda et al. | |
| 2009/0032770 A1 | | 2/2009 | Freitag et al. | |
| 2012/0121843 A1 | | 5/2012 | Lebel et al. | |

FOREIGN PATENT DOCUMENTS

| | | | |
|---|---|---|---|
| CA | 1335680 C | * | 5/1995 |
| EP | 0021213 A1 | | 7/1981 |
| JP | 46-019058 B | * | 5/1971 |
| JP | 53033992 B | * | 9/1978 |
| WO | WO 2007/022008 A2 | | 2/2007 |

OTHER PUBLICATIONS

Written Translation of JP 53-033992B. Sep. 18, 1978.*
Murano, M. and Hongo, T. Studies on the sequence of copolyesters by 31 P-NMR spectroscopy. Polymer Preprints (American Chemical Society, Division of Polymer Chemistry). 1978, vol. 19, pp. 256-260.*
Definition of oligomer. http://www.thefreedictionary.com/oligomer. As viewed on Mar. 26, 2015.*
Polyethylene Terephthalate (PET) Production and Manufacturing Process. ICIS. Nov. 6, 2007.*
Korshak, V. V.; Gribova, I. A.; Shitikov, V. K. Organophosphorus Polymers Communication 2. Polycondensation of Bis-2-chloroalkyl- and aryl-Phosphonates. Bulletin of the Academy of Sciences of the USSR, Division of Chemical Science. 1958, vol. 7, pp. 196-201.*
Fradat, A.; Tessier, M. Chapter 2: Polyesters. Section 2.1: Introduction. Synthetic Methods in Step-Growth Polymerization. 2003. John Wiley & Sons, Inc. pp. 17-18.*
Definition of "bis-". Hawley's Condensed Chemical Dictionary. Mar. 15, 2007. John Wiley & Sons, Inc.*
Written Translation of JP46-019058B. May 28, 1971.*
International Search Report dated Oct. 11, 2013 received for corresponding PCT/US2013/048892.
Cotter, Engineering Plastics: A Handbook of Polyarylethers, Gordon and Breach Science Publishers S.A., Switzerland, (1995). (TOC).
Extended European Search report issued in European Patent Application No. 13808572.5 dated Feb. 19, 2016.

* cited by examiner

Primary Examiner — Robert C Boyle
Assistant Examiner — Stephen Rieth
(74) Attorney, Agent, or Firm — Pepper Hamilton LLP

(57) ABSTRACT

Polyester co-polyphosphonates including of phosphonates covalently incorporated with polyesters and methods for making such polyester co-polyphosphonates are described herein. The polyester co-phosphonates and compositions prepared from these compounds exhibit an excellent combination of processing characteristics, mechanical and fire resistant properties.

19 Claims, No Drawings

POLYESTER CO-PHOSPHONATES

CROSS-REFERENCE TO RELATED APPLICATIONS

This application claims priority to U.S. Provisional Application No. 61/666,005, entitled, "Flame Retardant Polyester Compositions Including Oligomeric Phosphonates and Methods for Their Preparation" filed Jun. 29, 2012, which is incorporated herein by reference in its entirety.

GOVERNMENT INTERESTS

Not applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not applicable

In general, it has been extremely challenging to impart fire resistance into polyester resins and fibers without detracting from other properties such as processability, ability to melt spin fibers, and mechanical properties. In addition, small molecule flame retardants can leach from the polyester and contaminate the environment, and as a result, certain flame retardants have been banned in several countries. Thus, there is a recognized need to provide fire resistance to polyester fibers in an environmentally friendly manner without detracting from melt processability, strength, modulus, dyeing and heat-setting characteristics as compared to the unmodified polyester.

Flame retardant polyesters must be resistant to degradation by residual acidic groups in the polyester, exhibit long-term dimensional stability, have good dyeing characteristics in the final fiber, and exhibit good mechanical properties. The requirements for flame retarding polyesters are stringent in part because of the high processing temperatures and sensitivity of the polyesters' physical properties such as melt viscosity to the addition of flame retardants. For example, small molecule flame retardants often increase the melt viscosity of the polyester which reduces the melt processability of the polyester making it more difficult to make fibers by melt spinning. These challenges combined with environmental regulations for toxicity and mitigation of leaching of the flame retardant into the environment over time have made it extremely difficult to meet all of these requirements.

SUMMARY OF THE INVENTION

Various embodiments of the invention are directed to polyester co-phosphonates and polymer blends including polyester co-phosphonates. In some embodiments, the polyester co-phosphonates may be of Formula Ia, Ib, Ic, or combinations thereof:

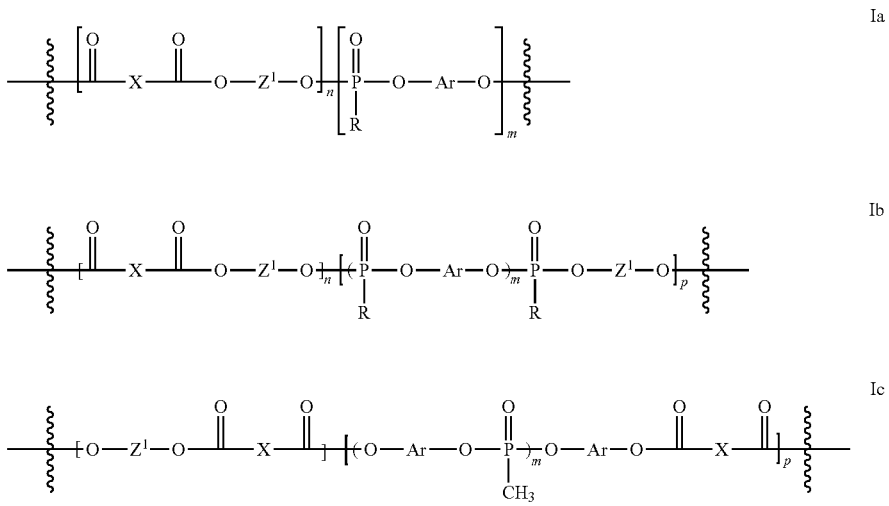

wherein each X is, independently, $C_{1-20}$ alkylene, $C_{2-20}$ alkenylene, $C_{2-20}$ alkynylene, $C_{5-20}$ cycloalkylene, or $C_{6-20}$ arylene; each $Z^1$ is, independently, $C_{1-20}$ alkylene, $C_{2-20}$ alkenylene, $C_{2-20}$ alkynylene, $C_{5-20}$ cycloalkylene, or $C_{6-20}$ arylene; each Ar is, independently, an aromatic group; each n is, independently, an integer from 1 to about 100; each m is, independently, an integer from 1 to about 20; and each p is, independently, an integer from about 1 to about 100.

In certain embodiments, —O—Ar—O— may be derived from a dihydroxy compound having one or more, optionally substituted aryl rings, and in some embodiments, —O—Ar—O— may be derived from a bisphenol selected from the group consisting of resorcinol, hydroquinone, 4,4'-biphenol, 2,2-bis(4-hydroxyphenyl)propane, 3,3'-biphenol, 4,4'-dihydroxyphenyl ether, 4,4'-dihydroxydiphenylsulfone, 9,9-dihydroxyphenyl fluorine, 1,1-bis(4-hydroxyphenyl)-3,3-dimethyl-5-methylcyclohexane, 4,4'-dihydroxybenzophenone, 4,4'-dihydroxyphenyl sulfide, 1-methyl-1-phenyl bis(4-hydroxyphenyl)methane, bis(3-hydroxyphenyl)methane, bis(4-hydroxyphenyl)methane, 9,9-bis(3-methyl-4-hydroxyphenyl)fluorene, 9,9-bis(3,5-dimethyl-4-hydroxyphenyl) fluorine, 1,4-bis[(4-hydroxyphenyl)-2-propyl]benzene, 1,4-bis[(4-hydroxyphenyl)-3,5 dimethylphenyl]-2-propyl] benzene, 4,4'-bis(4-hydroxyphenyl)diphenyl methane, 2,2-bis(4-hydroxyphenyl)hexafluoroisopropylidene, 1-trifluoromethyl-1-phenyl bis(4-hydroxyphenyl)methane, and combinations thereof. In particular embodiments,

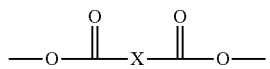

may be derived from a compound selected from the group consisting of adipic acid, terephthalic acid, isophthalic acid, naphthalene dicarboxylic acid, dimethyl terephthalate, dimethyl isophthalate, dimethyl naphthalate, and combinations thereof. In some embodiments, $Z^1$ may be a $C_{1-20}$ alkylene. In particular embodiments, X may be naphthalene or phenyl, $Z^1$ may be methylene, ethylene, propylene, butene, or pentene, and Ar may be derived from resorcinol, hydroquinone, or bisphenol A.

In other embodiments, the polyester co-phosphonate may be of Formula IVa and IVb:

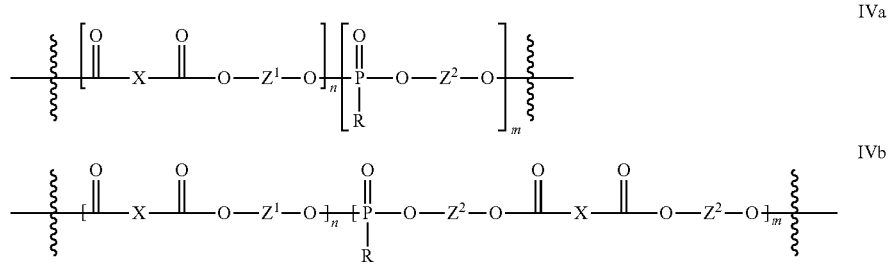

wherein each X is, independently, $C_{1-20}$ alkylene, $C_{2-20}$ alkenylene, $C_{2-20}$ alkynylene, $C_{5-20}$ cycloalkylene, or $C_{6-20}$ arylene; each $Z^1$ is, independently, $C_{1-20}$ alkylene, $C_{2-20}$ alkenylene, $C_{2-20}$ alkynylene, and $C_{5-20}$ cycloalkylene; each $Z^2$ is, independently, $C_{1-20}$ alkylene, $C_{2-20}$ alkenylene, $C_{2-20}$ alkynylene, and $C_{5-20}$ cycloalkylene; each n is, independently, an integer from 1 to about 100; and each m is, independently, an integer from 1 to about 100.

In some embodiments,

may be derived from a compound selected from the group consisting of adipic acid, terephthalic acid, isophthalic acid, naphthalene dicarboxylic acid, dimethyl terephthalate, dimethyl isophthalate, dimethyl naphthalate, and combinations thereof. In certain embodiments, $Z^1$ may be a $C_{1-20}$ alkylene, and in particular embodiments, $Z^2$ is a $C_{1-20}$ alkylene. In some embodiments, X may be naphthalene or phenyl and $Z^1$ and $Z^2$ may be independently methylene, ethylene, propylene, butene, or pentene.

Certain embodiments are directed to a composition including at least one polyester co-phosphonate of Formula Ia, Ib, Ic, as described above, or combinations thereof and/or at least one polyester co-phosphonate of Formula IVa, IVb, as described above, or combinations thereof. In some embodiments such compositions may further include one or more additives such as, but not limited to, talc, silica, clays, chopped or continuous glass fiber, metal fibers, organic fibers, aramid fibers, carbon fibers, carbon nanofibers, ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon black, graphite, graphene, graphene oxide, carbon nanotubes, carbon buckyballs, organic antistatics, polyalkylene ethers, alkylsulfonates, perfluoro sulfonic acid, perfluorbutane sulfoinic acid potassium salt, polyamide-containing polymers, catalysts, colorants, inks, dyes, antioxidants, stabilizers, metal phosphinates, melamine cyanurate, melamine derivatives, flame retardants, or combinations thereof. In particular embodiments, the compositions may include one or more engineering polymers, and in various embodiments, the one or more polymers may include, but are not limited to, polycarbonates, epoxies derived polymers, polyepoxies, benzoxazines, polyacrylates, polyacrylonitriles, polyesters, poly(ethylene terephthalate), poly(trimethylene terephthalate), and poly(butylene terephthalate), unsaturated polyesters, polyamides, polystyrenes, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, and cellulose polymers.

Further embodiments are directed to articles of manufacture including at least one polyester co-phosphonate of Formula Ia, Ib, Ic, as described above, or combinations thereof and/or at least one polyester co-phosphonate of Formula IVa, IVb, as described above, or combinations thereof. In some embodiments such compositions may further include one or more additives such as, but not limited to, talc, silica, clays, chopped or continuous glass fiber, metal fibers, organic fibers, aramid fibers, carbon fibers, carbon nanofibers, ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon black, graphite, graphene, graphene oxide, carbon nanotubes, carbon buckyballs, organic antistatics, polyalkylene ethers, alkylsulfonates, perfluoro sulfonic acid, perfluorbutane sulfonic acid potassium salt, polyamide-containing polymers, catalysts, colorants, inks, dyes, antioxidants, stabilizers, metal phosphinates, melamine cyanurate, melamine derivatives, flame retardants, or combinations thereof. In particular embodiments, the compositions may include one or more engineering polymers, and in various embodiments, the one or more engineering polymers may include, but are not limited to, polycarbonates, epoxies derived polymers, polyepoxies, benzoxazines, polyacrylates, polyacrylonitriles, polyesters, poly(ethylene terephthalate), poly(trimethylene terephthalate), and poly(butylene terephthalate), unsaturated polyesters, polyamides, polystyrenes, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, and cellulose polymers.

The type of article of manufacture including the polyester co-phosphonates described above is not limited, and in certain embodiments, the article may be selected from, for example, injection molded articles, bottles, extruded sheets, films, tarpaulin, canoes, liquid crystal displays, holograms, filters, dielectric films, insulation for wires, insulating tapes, packaging materials, protective materials, films, and moldings. In some embodiments, the article may be selected from fibers, fabrics, yarns, woven and non-woven goods. In particular embodiments, the article may be household furnishings. In some embodiments, the article may be carpet, upholstery, fabrics, clothing, ropes, and belts.

Further embodiments are directed to methods for preparing a polyester co-phosphonate including the steps of combining at least one diol and at least one dicarboxylic acid or at least one di-ester to form a reaction mixture; reacting the reaction mixture; and introducing at least one phosphonate into the reaction mixture, wherein the phosphonate is incorporated into a polyester to form a polyester co-phosphonate. In some embodiments, the method can be a batch process or a continuous process. In particular embodiments, the method may further include the step of adding at least one AB monomer into the reaction mixture. In various embodiments, the method may further include the step of introducing a catalyst into the reaction mixture. In some embodiments, the phosphonate can be about 1 wt. % to about 80 wt. % of the reaction mixture. In certain embodiments, the phosphonate can be a diaryl alkyl phosphonate, and in certain embodiments, the phosphonate can be diphenyl methyl phosphonate. In some embodiments, the phosphonate may be an oligomeric phosphonate, and in particular embodiments, the phosphonate may be an oligomeric phosphonate derived from diphenyl methyl phosphonate and bisphenol A. In certain embodiments, the phosphonate may be a polyphosphonate, and in some embodiments, the polyphosphonate may be derived from diphenyl methyl phosphonate and bisphenol A. In particular embodiments, incorporating may be carried out during the step of reacting, and in some embodiments, introducing can be carried out during or after the step of combining. In some embodiments, the diol may be selected from the group consisting of 1,4-cyclohexyldimethanol, 1,4-butane diol, 1,3-propane diol, ethylene diol, and combinations thereof, and in certain embodiments, the diol can be ethylene glycol. In other embodiments, the diol may be selected from the group consisting of 4,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)methane, bis(4-hydroxy-3,5-dimethylphenyl)methane, bis(4-hydroxy-3,5-dichlorophenyl)methane, bis(4-hydroxy-3,5-dibromophenyl)methane, bis(4-hydroxy-3-methylphenyl)methane, bis(4-hydroxy-3-chlorophenyl)methane, 1,1-bis(4-hydroxyphenyl)cyclohexane, bis(4-hydroxyphenyl)ketone, bis(4-hydroxy-3,5-dimethylphenyl)ketone, bis(4-hydroxy-3,5-dichlorophenyl)ketone, bis(4-hydroxyphenyl)sulfide, and bis(4-hydroxyphenyl)sulfone. In some embodiments, the at least one dicarboxylic acid or at least one di-ester may be selected from the group selected from adipic acid, terephthalic acid, isophthalic acid, naphthalene dicarboxylic acid, and combinations thereof. In certain embodiments, the at least one dicarboxylic acid or at least one di-ester may be selected from the group consisting of dimethyl terephthalate, dimethyl isophthalate, dimethyl naphthalate, and combinations thereof.

In some embodiments, the methods may further include introducing one or more additives into the polyester co-phosphonate, and in various embodiments, introducing the one or more additives into the polyester co-phosphonate can be carried out during or after reacting. In some embodiments, the method may further include pelletizing the polyester co-phosphonate. In other embodiments, the methods may further include spinning the polyester co-phosphonate into fibers, and in certain embodiments, such methods may include the step of heat setting the fibers. In some embodiments, the fibers or heat set fibers may be subjected to weaving the fibers into fabric or twisting the fibers into yarn. The methods of some embodiments may include the step of blending the polyester co-phosphonate with an engineering polymer such as, for example, polycarbonates, epoxies derived polymers, polyepoxies, benzoxazines, polyacrylates, polyacrylonitriles, polyesters, poly(ethylene terephthalate), poly(trimethylene terephthalate), and poly(butylene terephthalate), unsaturated polyesters, polyamides, polystyrenes, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, and cellulose polymers, and in some embodiments, the engineering polymer may be a polyester. In some embodiments, the method may further include mixing the polyester co-phosphonates with one or more additives such as, but not limited to, talc, silica, clays, chopped or continuous glass fiber, metal fibers, organic fibers, aramid fibers, carbon fibers, carbon nanofibers, ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon black, graphite, graphene, graphene oxide, carbon nanotubes, carbon buckyballs, organic antistatics, polyalkylene ethers, alkylsulfonates, perfluoro-sulfonic acid, perfluorbutane sulfonic acid potassium salt, polyamide-containing polymers, catalysts, colorants, inks, dyes, antioxidants, stabilizers, metal phosphinates, melamine cyanurate, melamine derivatives, flame retardants, or combinations thereof. In particular, embodiments, the methods may include the steps of spinning or twisting the polymer blends or additive containing polyester co-phosphonates or blends containing additives into fibers or yarns, respectively.

DESCRIPTION OF THE DRAWINGS

Not Applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention. The above summary of the present invention is not intended to describe each illustrated embodiment or every possible implementation of the present invention. The detailed description, which follows, particularly exemplifies these embodiments.

It must also be noted that, as used herein and in the appended claims, the singular forms "a," "an," and "the" include plural reference unless the context clearly dictates otherwise. Thus, for example, reference to "a combustion chamber" is a reference to "one or more combustion chambers" and equivalents thereof known to those skilled in the art, and so forth.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

The term "aliphatic diol" is meant to encompass any aliphatic or predominately aliphatic compound with at least two associated hydroxyl substitutions. Aliphatic diols may include telechelic ester oligomers with hydroxyl terminal groups or any telechelic oligomer with hydroxyl terminal groups, diol monomers such as 1,4-cyclohexyldimethanol, 1,4-butane diol, 1,3-propane diol, and ethylene diol. The diol functionality may be protected in the form of a trimethylsilyl group.

The term "aromatic diol" is meant to encompass any aromatic or predominately aromatic compound with at least two associated hydroxyl substitutions. In certain embodiments, the aromatic diol may have two or more phenolic hydroxyl groups. Examples of aromatic diols include, but are not limited to, 4,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl) propane, bis(4-hydroxyphenyl)methane, bis(4-hydroxy-3,5-dimethylphenyl)methane, bis(4-hydroxy-3,5-dichlorophenyl)methane, bis(4-hydroxy-3,5-dibromophenyl)methane, bis(4-hydroxy-3-methylphenyl) methane, bis(4-hydroxy-3-chlorophenyl)methane, 1,1-bis (4-hydroxyphenyl)cyclohexane, bis(4-hydroxyphenyl) ketone, bis(4-hydroxy-3,5-dimethylphenyl)ketone, bis(4-hydroxy-3,5-dichlorophenyl)ketone, bis(4-hydroxyphenyl) sulfide and bis(4-hydroxyphenyl)sulfone, phenolphthalein, 4,4'-thiodiphenol, 4,4'-sulfonyldiphenol, 4,4,-dihydroxydiphenyl ether or 3,3,5-trimethylcyclohexyldiphenol. In some embodiments, a single aromatic diol may be used, and in other embodiments, various combinations of such aromatic diols may be incorporated into the polyester. In certain embodiments, the aromatic diol may be bisphenol A, bisphenol F, hydroquinone, resorcinol, 2,6-dihydroxynaphthalene, 1,1-bis(4-hydroyphenyl)-3,3,5-trimethyl-cyclohexane (TMC bisphenol) and bis(4-hydroxyphenyl)sulfone, can be used. In further embodiments, the diol functionality may be in the form of a trimethylsilyl group.

Polyesters can be synthesized using AB monomers. The term "AB monomer" is meant to encompass any difunctional monomers that can react to form a polyester. Examples include but are not limited to, hydroxycarboxylic acids or derivatives thereof (i.e. acid halides, esters, anhydrides) with at least one each of a hydroxyl or protected hydroxyl group and a carboxylic acid, ester, acid halide or other carboxylic acid derivative group. Examples may include but are not limited to, para-hydroxybenzoic acid, meta-hydroxybenzoic acid, 2-hydroxy-6-naphthoic acid, 2-hydroxy-3-naphthoic acid, 1-hydroxy-4-naphtholic acid, 4-hydroxy-4'-carboxydiphenyl ether, 2,6-dichloro-para-hydroxybenzoic acid, 2-dichloro-para-hydroxybenzoic acid, 2,6-difluoro-para-hydroxybenzoic acid and 4-hydroxy-4'-biphenylcarboxylic acid. As with the aromatic and aliphatic diols, these compounds may be used individually or in a combination of two or more different aromatic hydroxycarboxylic acids. In certain embodiments, the aromatic hydroxycarboxylic acid may be para-hydroxybenzoic acid, 2-hydroxy-6-naphthoic acid, or a combination thereof. Additional AB monomers can include cyclic lactones such as caprolactone and others, lactides such as lactide and others. The AB monomers can be used alone, combined with one another or used in combination with other monomers for polyester synthesis.

The term "dicarboxylic acid" is meant to encompass any aromatic or aliphatic compound with at least two associated carboxylic acid substitutions or derivatives of carboxylic acid groups such as anhydrides, esters, acid halides, and the like. Examples include, but are not limited to, adipic acid, dimethyl terephthalic acid, terephthalic acid, isophthalic acid, and naphthalene dicarboxylic acid or derivatives thereof. Derivatives may include dimethyl terephthalate, dimethyl isophthalate, and dimethyl naphthalate.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, napthyl, biphenyl ring systems and the like. The aryl group may be unsubstituted or substituted with a variety of substituents including but not limited to alkyl, alkenyl, halide, benzylic, alkyl or aromatic ether, nitro, cyano and the like and combinations thereof.

"Substituent" refers to a molecular group that replaces a hydrogen in a compound and may include but are not limited to trifluoromethyl, nitro, cyano, $C_1$-$C_{20}$ alkyl, aromatic or aryl, halide (F, Cl, Br, I), $C_1$-$C_{20}$ alkyl ether, $C_1$-$C_{20}$ alkyl ester, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH substituent on the aryl ring. Non-limiting examples of an arylol are phenol, naphthol, and the like. A wide variety of arylols may be used in the embodiments of the invention and are commercially available.

The term "alkanol" or "alkanol group" refers to a compound including an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkenol" or "alkenol group" refers to a compound including an alkene 2 to 20 carbon atoms or more having at least one hydroxyl group substituent. The hydroxyl may be arranged in eitherisomeric configuration (cis or trans). Alkenols may be further substituted with one or more substituents as described above and may be used in place of alkenols in some embodiments of the invention. Alkenols are known to those skilled in the art and many are readily available commercially.

As used herein, the term "about" means plus or minus 10% of the numerical value of the number with which it is being used. Therefore, about 50% means in the range of 45%-55%.

The terms "flame retardant," "flame resistant," "fire resistant," or "fire resistance," as used herein, means that the composition exhibits a limiting oxygen index (LOI) of at least 27. "Flame retardant," "flame resistant," "fire resistant," or "fire resistance," may also refer to the flame reference standard ASTM D6413-99 for textile compositions, flame persistent test NF P 92-504, and similar standards for flame resistant fibers and textiles. Fire resistance may also be tested by measuring the after-burning time in accordance with the UL test (Subject 94). In this test, the tested materials are given classifications of UL-94 V-0, UL-94 V-1 and UL-94 V-2 on the basis of the results obtained with the ten test specimens. Briefly, the criteria for each of these UL-94-V-classifications are as follows:

UL-94 V-0 the average burning and/or glowing time after removal of the ignition flame should not exceed 10 seconds and none of the test specimens should release any drips which ignite absorbent cotton wool.

UL-94 V-1: the average burning and/or glowing time after removal of the ignition flame should not exceed 30 seconds and none of the test specimens should release any drips which ignite absorbent cotton wool.

UL-94 V-2: the average burning and/or glowing time after removal of the ignition flame should not exceed 30 seconds and the test specimens release flaming particles, which ignite absorbent cotton wool.

Fire resistance may also be tested by measuring afterburning time. These test methods provide a laboratory test procedure for measuring and comparing the surface flammability of materials when exposed to a prescribed level of radiant heat energy to measure the surface flammability of materials when exposed to fire. The test is conducted using small specimens that are representative, to the extent possible, of the material or assembly being evaluated. The rate at which flames travel along surfaces depends upon the physical and thermal properties of the material, product or assembly under test, the specimen mounting method and orientation, the type and level of fire or heat exposure, the availability of air, and properties of the surrounding enclosure. If different test conditions are substituted or the end-use conditions are changed, it may not always be possible by or from this test to predict changes in the fire-test-response characteristics measured. Therefore, the results are valid only for the fire test exposure conditions described in this procedure. The state-of-the-art approach to rendering polyesters flame retardant is to use additives such as brominated compounds or compounds containing aluminum and/or phosphorus. Use of the additives with polyesters has a deleterious effect on the processing characteristics and/or the mechanical performance of fibers produced from them. In addition, some of these compounds are toxic and can leach into the environment over time making their use less desirable. In some countries, certain brominated additives and aluminum and/or phosphorus containing additives are being phased-out of use because of environmental concerns.

The term "toughness," as used herein, is meant to imply that the material is resistant to breaking or fracturing when stressed or impacted. There are a variety of standardized tests available to determine the toughness of a material. Generally, toughness is determined qualitatively using a film or a molded specimen.

The phrase "low viscosity when sheared," "shear thinning," or similar phrases, as used herein, is meant to imply that when the material is melted and subjected to a shearing force, such as that encountered with certain types of mixers or when the melt is forced with pressure through a die or body having similar orifice, the viscosity is reduced. Shear thinning behavior may be transferred to blends of materials. Shear thinning can be measured using standardized methods such as the Shear Thinning Index (STI). STI represents the ratio of the viscosity at a low rpm shear to the viscosity at a high rpm, generally, about ten times the low rotational speed. For example, low shear may be 1 rpm and high shear can be 10 rpm. The higher the STI value, the more shear thinning the material exhibits.

The term "fiber" means a monofilament or multi-filament continuous or chopped strand of any diameter and shape fabricated by any known method from a polymeric composition.

"Number averaged molecular weight" can be determined by relative viscosity ($\eta_{rel}$) and/or gel permeation chromatography (GPC). Unless otherwise indicated, the values recited are passed on polystyrene standards. Relative viscosity ($\eta_{rel}$) is a measurement that is indicative of the molecular weight of a polymer and is generally measured dissolving a known quantity of polymer in a solvent and comparing the time it takes for this solution and the neat solvent to travel through a capillary (i.e., viscometer) at a constant temperature. It is also well known that a low relative viscosity is indicative of a low molecular weight polymer. Low molecular weight may causes mechanical properties such as strength and toughness to be worse compared to higher molecular weight high relative viscosity polymers. Therefore, reducing the relative viscosity of a polymer would be expected to result in a reduction in mechanical properties, for example, poor strength or toughness compared to a higher relative viscosity polymer having the same composition.

GPC is a type of chromatography that separates polymers by size. This technique provides information about the molecular weight and molecular weight distribution of the polymer, i.e., the polydispersity index (PDI).

Embodiments of the invention are directed to flame retardant polyester compositions that include polyesters having at least one phosphonate covalently integrated into the polyester. Such compounds will be generally referred to as "polyester co-phosphonates" herein. In some embodiments, units derived from phosphonate monomers can be randomly incorporated into a polyester to create "random polyester co-phosphonates." In other embodiments, one or more units derived from phosphonate monomers can be incorporated between oligomeric or polymeric polyester components covalently linking the oligomeric or polymeric phosphonate components. In such embodiments, the number of contiguous units derived from phosphonate monomers may be small, for example, from 1 to about 5, to create "phosphonate linked polyester co-phosphonates," or in other embodiments, the number of contiguous units derived from phosphonate monomers may be greater than 5, for example, from about 5 to about 20 or about 5 to about 10, to create "block polyester co-phosphonates." In embodiments including contiguous units derived from phosphonate monomers, the phosphonate units may be linked to one another by aliphatic units derived from, for example, linear or branched aliphatic diols, linear or branched aliphatic polyols, or cyclo-aliphatic diols or polyols. Such linear or branched aliphatic diols, linear or branched aliphatic polyols, or cyclo-aliphatic diols or polyols are more fully described below. In other embodiments, contiguous units derived from phosphonate monomers can be linked to one another by aromatic diols or polyols such as, for example, bisphenols. Such aromatic diols and polyols are described more fully below.

Other embodiments are directed to compositions that include polyester and oligomeric phosphonates. In such embodiments, the oligomeric phosphonates may be covalently incorporated into the polyester, i.e., a block polyester co-phosphonate as described above, or in other embodiments, the oligomeric phosphonates may be mixed with the polyester component of the mixture to produce a mixture of separate oligomeric phosphonates and polyester component. In still other embodiments, a portion of the oligomeric phosphonate may be incorporated into the polyester as a block polyester co-phosphonate and another portion of the oligomeric phosphonate may be separate from the block polyester co-phosphonate as to create a mixture of oligomeric phosphonate and block polyester co-phosphonate. In yet other embodiments, oligomeric phosphonates can be mixed with random polyester co-phosphonates, phosphonate linked polyester co-phosphonates, or combinations of random polyester co-phosphonates, phosphonate linked polyester co-phosphonates, and block polyester co-phosphonates.

In some embodiments, oligomeric phosphonates are incorporated into the main chain of the polyester by covalent linkages to create block polyester co-phosphonate. Such compositions are not admixtures of polyester and the flame retardant oligomeric phosphonates. These polyester co-phosphonates exhibit excellent flame retardancy, good mechanical properties, excellent melt spinnability, and no leaching of oligomeric phosphonate.

For simplicity, throughout this disclosure, the terms, "oligomeric phosphonates," "phosphonate oligomers," and the like are to be construed as referring to any oligomeric phosphonate, oligomeric random copoly(phosphonate carbonate), or oligomeric block copoly(phosphonate carbonate) described below including linear, branched, indicating a relatively small number of branches, for example, 1 to about 5 branches per oligomer, or hyperbranched, indicating a relatively high number of branches, for example, greater than 5. While individual types of oligomers may be called out in specific exemplary embodiments, any oligomeric phosphonate described herein can be used in any embodiment describing the use of an oligomeric phosphonate.

In certain embodiments, the block polyester co-phosphonates may be of general Formula Ia, Ib, or Ic:

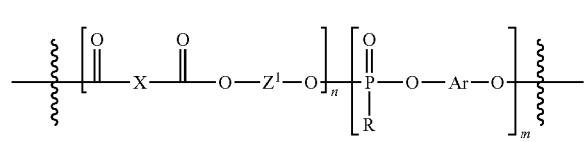

Ia

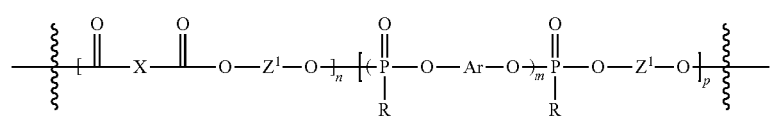

Ib

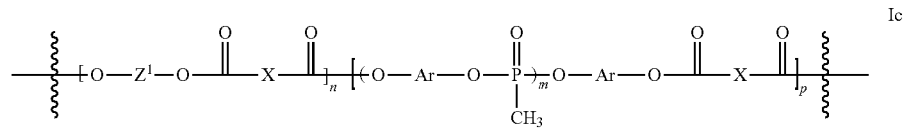

Ic where each X is, independently, a $C_{1-20}$ alkylene, $C_{2-20}$ alkylenylene, $C_{2-20}$ alkylynylene, $C_{5-20}$ cycloalkylene, or $C_{6-20}$ arylene, each $Z^1$ is, independently, $C_{1-20}$ alkylene, $C_{2-20}$ alkylenylene, $C_{2-20}$ alkylynylene, $C_{5-20}$ cycloalkylene, or $C_{6-20}$ arylene, each R is, independently, $C_{1-20}$ alkylene, $C_{2-20}$ alkylenylene, $C_{2-20}$ alkylynylene, $C_{5-20}$ cycloalkylene, or $C_{6-20}$ arylene, each Ar is, independently, an aromatic group, such as, for example, phenylene, biphenylene, propane-2,2-diyldibenzylene, naphthalene, and the like, and each —O—Ar—O— may, independently, be derived from a dihydroxy compound having one or more, optionally substituted aryl rings, and n, m, and p are each independently an integer from 1 to about 100, 1 to about 80, 1 to about 50, 1 to about 20, 1 to about 10, or 2 to about 5, or any integer between these ranges. In certain embodiments, the

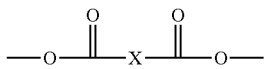

portion of the Formula I may be derived from adipic acid, dimethyl terephthalic acid, terephthalic acid, isophthalic acid, naphthalene dicarboxylic acid and the like or derivatives thereof or combinations thereof. In certain embodiments, X may be an aromatic group such as naphthalene, phenylene, biphenylene, propane-2,2-diyldibenzylene, and in some embodiments, X may be derived from, for example, dimethyl terephthalate, dimethyl isophthalate, dimethyl naphthalate, and the like and combinations thereof. Thus, X may be, for example, naphthalene, phenyl, both of which may be substituted at any position on the rings. In some embodiments, $Z^1$ can be a $C_{1-20}$ alkylene or cycloalkylene, such as methylene, ethylene, propylene, butylene, pentylene, and the like, and in particular embodiments, $Z^1$ can be derived from aliphatic diols such as, but not limited to, 1,4-cyclohexyldimethanol, 1,4-butane diol, 1,3-propane diol, ethylene diol, ethylene glycol, and the like and combinations thereof. In some embodiments, R may be methyl, and in other embodiments, R may be a substituted or unsubstituted arylene.

As it is difficult to draw copolymers without them appearing as discrete blocks, these structures are meant to represent copolymers that can be either random or block, or may contain a discrete block of one polymer or oligomer (for example ester) linked by a small molecule or oligomer of the other material type (for example, phosphonate).

In some embodiments, —O—Ar—O— may be derived from bisphenol. Such bisphenols may include, but are not limited to, 44,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)methane, bis(4-hydroxy-3,5-dimethylphenyl)methane, bis(4-hydroxy-3,5-dichlorophenyl)methane, bis(4-hydroxy-3,5-dibromophenyl)methane, bis(4-hydroxy-3-methylphenyl)methane, bis(4-hydroxy-3-chlorophenyl)methane, 1,1-bis(4-hydroxyphenyl)cyclohexane, bis(4-hydroxyphenyl)ketone, bis(4-hydroxy-3,5-dimethylphenyl)ketone, bis(4-hydroxy-3,5-dichlorophenyl)ketone, bis(4-hydroxyphenyl)sulfide and bis(4-hydroxyphenyl)sulfone, phenolphthalein, 4,4'-thiodiphenol, 4,4'-sulfonyldiphenol, 4,4-dihydroxydiphenyl ether or 3,3,5-trimethylcyclohexyldiphenol, and combinations thereof. In particular embodiments, the oligomeric phosphonates may include units derived from resorcinol, hydroquinone, or bisphenol A.

In some embodiments, the oligomeric phosphonate or portions thereof may include units of Formula II:

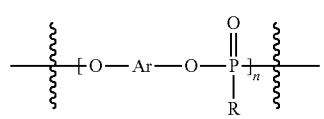

in which Ar is an aromatic group and —O—Ar—O— is derived from or bisphenol, R is a $C_{1-20}$ alkylene, $C_{2-20}$ alkylenylene, $C_{2-20}$ alkylynylene, $C_{5-20}$ cycloalkylene, or $C_{6-20}$ arylene, and n is an integer from 1 to about 10. In such embodiments, —O—Ar—O— may be derived from 4,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)methane, bis(4-hydroxy-3,5-dimethylphenyl)methane, bis(4-hydroxy-3,5-dichlorophenyl)methane, bis(4-hydroxy-3,5-dibromophenyl)methane, bis(4-hydroxy-3-methylphenyl)methane, bis(4-hydroxy-3-chlorophenyl)methane, 1,1-bis(4-hydroxyphenyl)cyclohexane, bis(4-hydroxyphenyl)ketone, bis(4-hydroxy-3,5-dimethylphenyl)ketone, bis(4-hydroxy-3,5-dichlorophenyl)ketone, bis(4-hydroxyphenyl)sulfide and bis(4-hydroxyphenyl)sulfone, phenolphthalein, 4,4'-thiodiphenol, 4,4'-sulfonyldiphenol, 4,4,-dihydroxydiphenyl ether or 3,3,5-trimethylcyclohexyldiphenol, or combinations thereof. Thus, in some embodiments, Ar in Formula Ia, Ib, Ic, and II may be derived from a bisphenol such as, resorcinol, hydroquinone, or bisphenol A to produce a block polyester co-phosphonate may be of general Formula III:

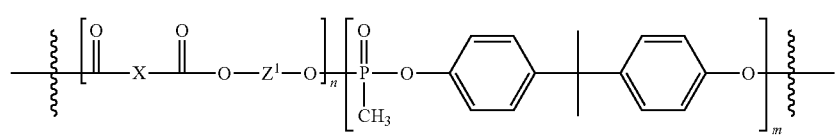

where X, $Z^1$, n and m are as described above.

In some embodiments, the polyester co-phosphonate may be of general Formula IVa, ans IVb:

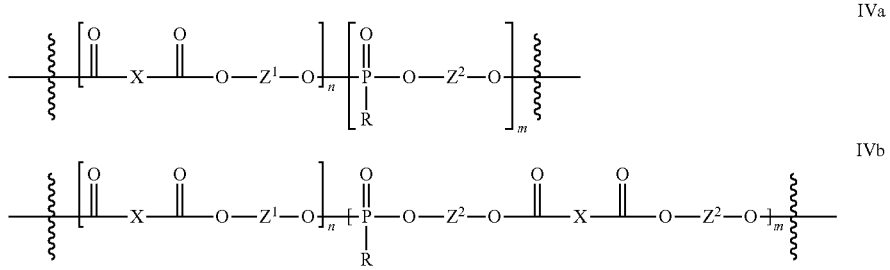

where each X is, independently, a $C_{1-20}$ alkylene, $C_{2-20}$ alkylenylene, $C_{2-20}$ alkylynylene, $C_{5-20}$ cycloalkylene, or $C_{6-20}$ arylene, each $Z^1$ and each $Z^2$ are, independently, $C_{1-20}$ alkylene, $C_{2-20}$ alkylenylene, $C_{2-20}$ alkylynylene, $C_{5-20}$ cycloalkylene, or $C_{6-20}$ arylene, each R is, independently, $C_{1-20}$ alkylene, $C_{2-20}$ alkylenylene, $C_{2-20}$ alkylynylene, $C_{5-20}$ cycloalkylene, or $C_{6-20}$ arylene, and n is an integer from 1 to about 100, 1 to about 80, 1 to about 50, 1 to about 20, 1 to about 10, or 2 to about 5, or any integer between these ranges. In certain embodiments, the

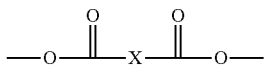

portion of the Formula III may be derived from adipic acid, dimethyl terephthalic acid, terephthalic acid, isophthalic acid, naphthalene dicarboxylic acid and the like or derivatives thereof or combinations thereof. In certain embodiments, X may be an aromatic group, and in some embodiments, X may be derived from, for example, dimethyl terephtalate, dimethyl isophtalate, dimethyl naphthalate, and the like and combinations thereof. Thus, X may be, for example, naphthalene, phenyl, both of which may be substituted at any position on the rings. In some embodiments, each $Z^1$ and each $Z^2$ can, independently, be a $C_{1-20}$ alkylene or cycloalkylene, such as methylene, ethylene, propylene, butylene, pentylene, and the like, and in particular embodiments, $Z^1$ and $Z^2$ can, independently, be derived from aliphatic diols such as, but not limited to, 1,4-cyclohexyldimethanol, 1,4-butane diol, 1,3-propane diol, ethylene diol, ethylene glycol, and the like and combinations thereof. In some embodiments, R may be methyl, and in other embodiments, R may be a substituted or unsubstituted arylene The polyester co-phosphonate of general Formulae Ia, Ib, Ic, IVa and IVb can encompass random polyester co-phosphonates, block polyester co-phosphonates, and phosphonate linked polyester co-phosphonates. In various embodiments, portions of one type of polyester co-phosphonate may exhibit the characteristics of another type of polyester co-phosphonate. For example, portions of a block polyester co-phosphonate may exhibit the characteristics of a random polyester co-phosphonate where a polyester or phosphonate block is shorter than the other blocks in the polyester co-phosphonates. Such polymers are encompassed by the invention. In some embodiments, the compounds illustrated as in Formulae Ia, Ib, Ic, IVa and IVb may be randomized during transesterification such that discrete, well-defined blocks are not present in the final copolymer. For example, if a polymeric or oligomeric ester is the starting material and a phosphonate oligomer is added during the reaction, the ester link in the polyester or oligoester may undergo transesterification leading to changes in the chemical structure of part of the ester backbone chain, thus the "block" would no longer be homogeneous.

The polymers of embodiments described above including polyester co-phosphonates of Formulae Ia, Ib, Ic, IVa, and IVb can have any end groups. For example, in various embodiments the polyester co-phosphonates may have end groups such as —OH, phenol, phenyl, ester, phosphoester, carboxyl, and the like. In some embodiments, each end group may be the same or different, and in embodiments in which the polyester co-phosphonates are branched the end group of each branch may be the same or different. For example, in some embodiments, substantially all of the end groups of the polyester co-phosphonates may be —OH. In other embodiments, a first portion of the end groups may be —OH, and a second portion of the end groups may be carboxyl or phenol.

The polyester co-phosphonates may include any amount of phosphorous. For example, the polyester co-phosphonates of various embodiments may have a phosphorous content of from about 0.1% to about 20% based on the total molecular polyester co-phosphonate, and the phosphorous content will vary depending on the type of polyester co-phosphonate, the size and number of units derived from phosphonate containing monomers, and the like. In particular embodiments, the phosphorous content based on the total molecular weight of the polyester co-phosphonate may be from about 0.5% to about 15%, about 1% to about 10%, about 1.5% to about 8%, about 2% to about 5%, or any individual amount or concentration range encompassed by these ranges. Notably, the phosphorous content of the polyester co-phosphonates of various embodiments can be substantially increased by incorporating a relatively small amount of a phosphonate containing monomer. For example, phosphonate blocks derived from a phosphonate source such as, for example, diphenyl methylphosphonate, and a diol such as, for example, ethylene glycol produce repeating units, referred to as "aliphatic phosphonate" units, having a phosphorous content of about 25%, whereas a phosphonate block derived from a phosphonate source such as diphenyl methylphosphonate and a bisphenol such as bisphenol A, referred to as "aromatic phosphonate" units, has a phosphorous content of about 10%. Therefore, to achieve polyester with equal phosphorous content less than half the amount of phosphonate can be incorporated by providing aliphatic phosphonate units.

Without wishing to be bound by theory, polyester co-phosphonates having higher phosphorous content but fewer phosphonate derived units may provide good flame retardancy, as a result of increased phosphorous content, while minimally disrupting the overall structure of the polyester providing similar physical properties as compared to polyesters having no phosphonate units. For example, in some embodiments, the polyester co-phosphonates may include about 1% to about 50% by weight phosphonate, and in other embodiments, the polyester co-phosphonates may be from about 2 wt. % to about 40 wt. %, about 5 wt. % to about 30 wt. %, about 10 wt. % to about 20 wt. %, or any individual amount or concentration range encompassed by these ranges. In such embodiments, substantially all of the remainder of the polyester co-phosphonate may be the polyester ester component. For example, a polyester co-phosphonate having about 1 wt. % phosphonate may have about 99 wt. % polyester component, and a polyester co-phosphonate having about 50 wt. % phosphonate may have about 50 wt. % polyester component.

In certain embodiments, all (i.e., 100%) of the oligomeric phosphonate may be covalently incorporated into the polyester co-phosphonate. In other embodiments, the amount of oligomeric phosphonate that has chemically reacted with and is covalently incorporated into the polyester co-phosphonates can be from about 5 wt. % to about 100%, about 20 wt. % to about 98 wt. %, about 50 wt. % to about 95 wt. %, about 65 wt. % to about 90 wt. % or any individual amount or concentration range encompassed by these ranges. In other embodiments, a portion of the oligomeric phosphonate in the polyester co-phosphonates may not be covalently incorporated into the polyester co-phosphonate but may remain in the composition as dissociated or free oligomeric phosphonate. In some embodiments, about 100% of the oligomeric phosphonate may be dissociated from the polyester, and in other embodiments, from about 5 wt. % to about 100%, about 20 wt. % to about 98 wt. %, about 50 wt. % to about 95 wt. %, about 65 wt. % to about 90 wt. % or any individual amount or concentration range encompassed by these ranges may be dissociated from the polyester in the compositions of the invention. In certain embodiments, the amount of dissociated oligomeric phosphonate may be small, for example, less than about 1 wt. %, from about 0.5 wt. % to about 15 wt. %, about 1 wt. % to about 10 wt. %, about 2 wt. % to about 5 wt. %, or any individual amount or concentration range encompassed by these ranges.

In some embodiments, oligomeric phosphonates incorporated into block polyester co-phosphonates may include carbonate components. In some embodiments, the carbonate component can be arranged within the oligomeric phosphonates randomly meaning that units derived from carbonate monomers are randomly dispersed among units derived from phosphonate monomers, referred to herein as "random oligomeric co-phosphonates." In certain embodiments, the random oligomeric co-phosphonates may include at least 20 mole percent high purity diaryl alkylphosphonate or optionally substituted diaryl alkylphosphonate based on the total amount of transesterification components, i.e., total diaryl alkylphosphonate and total diphenyl carbonate. Such random oligomeric co-phosphonates may be any random oligomeric co-phosphonates known in the art and include, for example, the random copoly(phosphonate carbonate)s described in U.S. Pat. No. 8,389,664, which is hereby incorporated by reference in its entirety. In other embodiments, the carbonate component can be arranged in blocks meaning that segments of contiguous carbonate units are distributed among segments of contiguous phosphonate derived units, referred to herein as "block oligomeric co-phosphonates," and in particular embodiments, each phosphonate and carbonate segments of the block oligomeric phosphonates may have a similar size. The block oligomeric co-phosphonates of such embodiments may, typically, have a single glass transition temperature ($T_g$). The block oligomeric co-phosphonates useful in embodiments may be any block oligomeric co-phosphonates known in the art. For example, the block oligomeric co-phosphonates may be those described in U.S. Pat. No. 7,645,850, which is hereby incorporated by reference in its entirety.

The phosphonate and carbonate content of the random oligomeric co-phosphonates and block oligomeric co-phosphonates may vary among embodiments, and embodiments are not limited by the phosphonate and/or carbonate content or range of phosphonate and/or carbonate content. For example, in some embodiments, the random oligomeric co-phosphonates and block oligomeric co-phosphonates may have a phosphorus content of from about 1 wt. % to about 20 wt. % of the total copoly(phosphonate carbonate), and in other embodiments, the phosphorous content of the random oligomeric co-phosphonates and block oligomeric co-phosphonates may be from about 2 wt. % to about 15 wt. %, about 2 wt. % to about 10 wt. %, about 5 wt. % to about 8 wt. %, or any individual amount or concentration range encompassed by these ranges.

The random oligomeric co-phosphonates and block oligomeric co-phosphonates may have a solution viscosity ($\eta_{rel}$) of from about 1.03 to greater than about 1.35 and may have a $T_g$ of from about 28° C. to about 107° C. In particular embodiments, the random oligomeric co-phosphonates may have a relative viscosity of from about 1.10 to about 1.40. In some embodiments, the random oligomeric co-phosphonates and block oligomeric co-phosphonates may be branched or linear and can be prepared with up to about 50 mol. % branching agent. In other embodiments, the random oligomeric co-phosphonates and block oligomeric co-phosphonates may have a molecular weight ($M_n$) of from about 2,000 g/mol to about 35,000 g/mol.

The random oligomeric co-phosphonates and block oligomeric co-phosphonates of various embodiments exhibit both a high molecular weight and a narrow molecular weight distribution (i.e., low polydispersity). For example, in some embodiments, the random oligomeric co-phosphonates and block oligomeric co-phosphonates may have a weight average molecular weight (Mw) of about 10,000 g/mole to about 100,000 g/mole as determined by $\eta_{rel}$ or GPC, and in other embodiments, the random oligomeric co-phosphonates and block oligomeric co-phosphonates may have a Mw of from about 12,000 to about 80,000 g/mole as determined by $\eta_{rel}$ or GPC. The narrow molecular weight distribution (i.e., Mw/Mn) of such random oligomeric co-phosphonates and block oligomeric co-phosphonates may be from about 2 to about 7 in some embodiments and from about 2 to about 5 in other embodiments.

Without wishing to be bound by theory, the use of high purity diaryl alkylphosphonate or optionally substituted diaryl alkylphosphonate, and in particular embodiments, high purity diphenyl methyl phosphonate (DPP), in the preparation of the random oligomeric co-phosphonates may provide improved properties over other random copolymers of the prior art. As used herein "high purity" is meant to infer that the diaryl alkylphosphonate or optionally substituted diaryl alkylphosphonate includes total acidic components of less than about 0.15% by weight, less than about 0.10% by weight, and in certain embodiments, less than about 0.05% by weight. Such acidic components are known in the art and may include, but are not limited to, phosphoric acid, phosphonic acid, methyl phosphonic acid, and methyl phosphonic acid mono phenylester. In some embodiments, the random copoly(phosphonate carbonate)s may include substantially no acidic component contaminants, and in other embodiments, the random copoly(phosphonate carbonate)s may include, for example, total acidic components of less than about 0.15% by weight, less than about 0.10% by weight, and in certain embodiments, less than about 0.05% by weight.

Such random oligomeric co-phosphonates prepared from high purity diaryl alkylphosphonate or optionally substituted diaryl alkylphosphonate may exhibit high molecular weight and narrow molecular weight distribution, which in-turn, may impart a superior combination of properties. For example, such random oligomeric co-phosphonates are generally tough, extremely flame retardant, and exhibit superior hydrolytic stability. In addition, the random oligomeric co-phosphonates exhibit an excellent combination of processing characteristics including, for example, good thermal and mechanical properties.

Block oligomeric co-phosphonates can include carbonate components that are either commercially available or custom synthesized branched or linear polycarbonates. Non-limiting examples of commercially available polycarbonates may be those available under the trade names Lexan (General Electric Company), Makrolon (Bayer AG), Apec (Bayer AG), Hiloy (ComAlloy), Calibre (Dow Chemical Co.), Lupilonx (Mitsubishi), Naxell (MRC Polymers), Edgetek (PolylOne), Trirex (Kasei) and Panlite (Teijin Chemicals). Custom polycarbonates used as the carbonate component of the block oligomeric co-phosphonates may be prepared by any method known in the art. For example, custom polycarbonates may be synthesized from diphenyl carbonate and any known bisphenol using a transesterification catalyst, and in the case of branched polycarbonates, a branching agent, or by an interfacial polycondensation process using phosgene and any bisphenol with or without a branching agent. A variety of bisphenols can be used in such reactions, and a compilation of known bisphenols readily available and well known to those skilled in the art including those containing heterocyclic structures can be found in "Engineering Plastics: A Handbook of Polyarylethers" by Robert J. Cotter, Gordon and Breach Science Publishers S.A., Switzerland 1995. For example, bisphenols may include, but are not limited to, 4,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)methane, bis(4-hydroxy-3,5-dimethylphenyl)methane, bis(4-hydroxy-3,5-dichlorophenyl)methane, bis(4-hydroxy-3,5-dibromophenyl)methane, bis(4-hydroxy-3-methylphenyl)methane, bis(4-hydroxy-3-chlorophenyl)methane, 1,1-bis(4-hydroxyphenyl)cyclohexane, bis(4-hydroxyphenyl)ketone, bis(4-hydroxy-3,5-dimethylphenyl)ketone, bis(4-hydroxy-3,5-dichlorophenyl)ketone, bis(4-hydroxyphenyl)sulfide and bis(4-hydroxyphenyl)sulfone, phenolphthalein, 4,4'-thiodiphenol, 4,4'-sulfonyldiphenol, 4,4,-dihydroxydiphenyl ether or 3,3,5-trimethylcyclohexyldiphenol, and combinations thereof. In some embodiments the carbonate components may have a relative viscosity ($\eta_{rel}$) of at least about 1.2 or from about 1.02 to about 1.2.

The polyester component of the polyester co-polyphosphonates of the invention may be derived from any polyester, and the polyester component may be aromatic polyester, aliphatic polyester, aromatic and aliphatic co-polyesters, semi-aromatic polyesters, and combinations thereof. In certain embodiments, the polyester may be a known polyester such as, but not limited to, Polyglycolide or Polyglycolic acid (PGA), Polylactic acid (PLA), Polycaprolactone (PCL), Polyethylene adipate (PEA), Polyhydroxyalkanoate (PHA), Polyhydroxybutyrate (PHB), Poly(3-hydroxybutyrate-co-3-hydroxyvalerate) (PHBV), Polyethylene terephthalate (PET), Polybutylene terephthalate (PBT), Polytrimethylene terephthalate (PTT), Polyethylene Terephtalate Glycol-modified (PETG), Polyethylene naphthalate (PEN), Vectran, and the like and combinations thereof. Other polyesters and copolyesters, telechelic ester oligomers having hydroxyl, ester or carboxylic acid or derivatives thereof endgroups not specifically described are also encompassed by these embodiments and can be combined with the various phosphonate components described above to create the polyester co-polyphosphonates of the invention.

The polyester co-polyphosphonates of various embodiments described above can be prepared by any method, and such methods can be continuous or discontinuous. In various embodiments, the polyester portion of the polyester co-polyphosphonate can be prepared by transesterification and polycondensation processes often utilizing a catalyst to drive the reaction and produce high molecular weight polyester co-polyphosphonates. Such methods may typically include the steps of combining one or more di-carboxylic acid monomers with one or more diol monomers and adding a catalyst to this polyester reaction mixture. The one or more di-carboxylic acid monomers can be any of the di-carboxylic acid monomers described above, and the one or more diol monomers may be any of the aliphatic or aromatic diol monomers described above. In particular embodiments, the methods may include the step of modifying the di-carboxylic acid monomers to create di-methyl-ester monomers. Such modifying steps can be carried out by combining the di-carboxylic acid monomers with an alcohol containing reagent such as, for example, methanol. In other embodiments, a commercially available di-methyl-ester may be incorporated into the reaction mixture in place of or in combination with the di-carboxylic acid component. Without wishing to be bound by theory, the use of di-methyl-ester monomers may allow for improved polymerization by reducing hydrolysis of the polymer chain caused by the production of water during condensation as polymerization occurs.

Phosphonate monomers can be added to the reaction mixture during the transesterification and polycondensation processes as polymerization continues allowing the phosphonate monomers to be incorporated into the polyester. In such embodiments, the phosphonate monomers such as bisphenols may react with diol monomers or ends of polyester chains having a —OH end group covalently adding the phosphonate monomer to the growing polyester. The phosphonate monomer can then react with another diol monomer or a diol monomer associated with the phosphonate monomer can react with a di-carboxylic acid or di-methyl ester monomer incorporating the phosphonate into the polyester by covalent linkages.

In other embodiments, an oligomeric phosphonate, random oligomeric co-phosphonates or block oligomeric co-phosphonates, or combinations thereof having reactive end groups may be incorporated into the polyester reaction mixture during polymerization. The oligomeric phosphonate, random oligomeric co-phosphonates or block oligomeric co-phosphonates can react with the other components of these mixtures during the transesterification or polycondensation and become incorporated into the polyester creating a polyester co-phosphonate and imparting flame retardancy on the polyester and any product produced from the polyester.

In various embodiments, polyester synthesis may involve any one of the following processes.

In the transesterification method, a diol or an alcohol-terminated oligomer and a di-acid, or ester monomer or an acid-terminated or ester-terminated oligomer are heated in the melt to condense to form an ester linkage with water or alcohol being a by-product. This can also be conducted using an AB monomer. Typically a catalyst is used; examples of catalysts include, but are not limited to, antimony trioxide.

Polycondensation involves placing the diol and dicarboxylic acid or derivative thereof in a reaction vessel and heating the mixture to melting. For polymer formation to occur, the water or alcohol generated from the reaction must be continually removed by azeotropic distillation. In the acyl halide method, the dicarboxylic acid is in the form of a diacid chloride, and the polycondensation is often conducted in a solvent with the emission of hydrogen chloride. In the silyl method, the diol is in the form of a di(trimethyl silyl ether) and the dicarboxylic acid is in the form of a diacid chloride, and the polycondensation is often conducted in a solvent with the emission of trimethyl silyl chloride.

Polyesters can also be synthesized by ring opening polymerization. For example, aliphatic polyesters can be prepared from lactones under very mild conditions, catalyzed anionically, cationically, or metallorganically. A number of catalytic methods for the copolymerization of epoxides with cyclic anhydrides have also been shown to provide a wide array of functionalized polyesters, both saturated and unsaturated. Various embodiments encompass all of the known polyester synthesis methods.

The polyester portion of the polyester co-polyphosphonates can be synthesized using a wide variety of monomer combinations. For example, the polyester portion can be prepared from one or more diols and one or more dicarboxylic acids or derivatives thereof, and in certain embodiments, the polyester portion can be prepared using an AB monomer such as 4-hydroxybenzoic acid or caprolactone. In other embodiments, the polyester portion can be prepared from a combination of one or more diols, one or more dicarboxylic acids or derivatives thereof and an AB monomer.

The monomers can be provided to the reaction mixture in any order, and any ratio of monomers can be used to make the polyester portion of the polyester co-polyphosphonates. For example, in some embodiments, the method for preparing polyester co-phosphonates may include the steps of combining at least one diol, at least one dicarboxylic acid, di-ester, or derivative thereof, and at least one phosphonate or oligomeric phosphonate to create a reaction mixture. In other embodiments, such methods may include the steps of combining at least one AB monomer at least one diol, at least one dicarboxylic acid or derivative thereof, and at least one oligomeric phosphonate to create a reaction mixture. In still other embodiments, the methods for preparing polyester co-phosphonates may include the step of combining at least one AB monomer with an oligomeric phosphonate under transesterification conditions. In such embodiments, the diol and the dicarboxylic acid, di-ester or derivative thereof may be aromatic, aliphatic, or a combination thereof and may contain non-carbon atoms such as bromine, fluorine, silicon, and the like and combinations thereof. In particular embodiments, the reaction mixtures described above may further include a catalyst such as, for example, antimony trioxide.

The phosphonate monomers or oligomeric phosphonates may be incorporated during any stage of the transesterification of the monomers, ester oligomer or polyester, and introduction of the oligomeric phosphonate should occur when a sufficient amount of oligomeric phosphonate can be incorporated into the polyester to provide good flame retardancy without disturbing the physical properties of the polyester. For example, in some embodiments, the phosphonate monomers or oligomeric phosphonate may be combined with the at least one diol, at least one dicarboxylic acid, di-ester, or derivative thereof, and optionally an AB monomer under conditions that allow for polymerization of the various components. In some embodiments, the phosphonate monomers or oligomeric phosphonate may be introduced into the reaction mixture prior to the initialization of transesterification, and in other embodiments, the phosphonate monomers or oligomeric phosphonate may be introduced into the reaction mixture after transesterification has been initiated and polymerization of the polyester monomers has been initiated. For example, in some embodiments, the phosphonate monomers or oligomeric phosphonates may be introduced into a reaction mixture after the transesterification of the at least one diol, at least one dicarboxylic acid or derivative thereof, and optionally an AB monomer or a combination thereof has gone to 1% to about 75% completion. In particular embodiments, transesterification of the at least one diol, at least one dicarboxylic acid, di-ester, or derivative thereof, optionally an AB monomer may have been initiated and transesterification of the polyester may be carried out until transesterification of the polyester components has gone to about 1%, 5%, 10%, 15%, 20%, 25%, 30%, 40%, 50%, 60%, or 75% completion before the phosphonate monomer of oligomeric phosphonate is added to the reaction mixture.

Reacting can be carried out by any method known in the art. In some embodiments, reacting can be carried out in the melt, and in other embodiments, reacting can be carried out using a solvent under elevated temperature. In certain embodiments, reacting may can carried out at reduced or elevated pressure and an inert atmosphere gas such as nitrogen or argon. In particular embodiments, transesterification can be carried out at a temperature of about 130° C. to about 180° C., and in other embodiments the reaction can be carried out at a temperature of 140° C. to 160° C. In certain embodiments, transesterification can be carried out under pressure greater or less than 1 atmosphere, and in some embodiments, the transesterification may be carried out under a vacuum to allow for removal of volatile by-products.

In some embodiments, the methods may be conducted under an inert atmosphere to prevent oxidation or unwanted side reactions. The inert atmosphere may be vacuum (exclusion of oxygen), or an inert gas such as nitrogen or argon may be introduced into the reaction vessel.

Transesterification can be carried out for any time necessary to produce a suitable polyester. For example, in some embodiments, transesterification can be carried out for about 15 minutes to about 20 hours and in other embodiments, transesterification can be carried out for about 30 minutes to about 5 hours or any individual amount or concentration range encompassed by these ranges. In particular embodiments, transesterification can be carried out for a time periods such as, but not limited to, 30 minutes, 1 hour, 1.5 hours, 2 hours, 3 hours, 4 hours, 5 hours, 6 hours, 7 hours, 10 hours, 15 hours, or 20 hours or more.

In some embodiments, transesterification can be carried out in the presence of a catalyst, and the catalyst may be acidic, basic or neutral. Examples of the catalyst include, but are not limited to, heterocyclic organic based compounds containing two or more nitrogen atoms such as N,N-dimethylaminopyridine and 1-methylimidazole, and inorganic oxides such as antimony trioxide.

As indicated above, the methods of various embodiments can be carried out in a number of steps. For example, in some embodiments, the method may include the step of combining at least one diol, at least one dicarboxylic acid or di-ester, and optionally at least one AB monomer or a combination thereof, and a phosphonate monomer or oligomeric phosphonate to form a reaction mixture and reacting the mixture components to form a polyester co-phosphonate. In other embodiments, the method may include the steps of combining at least one diol, at least one dicarboxylic acid or di-ester, and optionally at least one AB monomer or a combination thereof, to form a reaction mixture, initiating transesterification of the polyester reaction mixture, and introducing a phosphonate monomer or oligomeric phosphonate into the polyester reaction mixture to create a second reaction mixture as transesterification occurs. In still other embodiments, the method may include the steps of combining at least one diol, at least one dicarboxylic acid or di-ester, and optionally at least one AB monomer or a combination thereof, to form a polyester reaction mixture, reacting the polyester reaction mixture, stopping reacting of the polyester reacting mixture when oligomeric esters are formed, introducing a phosphonate monomer or oligomeric phosphonate into a reaction mixture including the oligomeric ester, and reacting the phosphonate monomer or oligomeric phosphonate and the oligomeric ester to produce the polyester co-phosphonate.

The amount of phosphonate monomer or oligomeric phosphonate included in the reaction mixtures or introduced into the reaction during transesterification may vary among embodiments, and any amount that provides sufficient flame retardancy may be used. For example, in some embodiments, the amount of phosphonate monomers or oligomeric phosphonate included may be about 0.25 wt. % to 80 wt. % based on the total reaction mixture. In other embodiments, the amount of phosphonate monomers or oligomeric phosphonate may be about 1 wt. % to about 30 wt. %, and in still other embodiments, the amount of phosphonate monomers or oligomeric phosphonate may be from about 2 wt. % to about 25 wt. %. Of course, the amount of phosphonate monomers or oligomeric phosphonate included during the methods described herein may be any amount between these exemplary ranges. For example, the amount of phosphonate monomers or oligomeric phosphonate included during the methods may be about 1 wt. %, about 2, wt. %, about 3 wt. %, about 5 wt. %, about 7 wt. %, about 10 wt. %, about 15, wt. %, about 20 wt. %, about 25 wt. %, about 30 wt. %, or about 50 wt. %. The amount of phosphonate monomers or oligomeric phosphonate that has chemically reacted with the ester monomers and oligomers can range from about 5% to about 100%. In some embodiments, the compositions of a polyester and a phosphonate monomers or phosphonate oligomer may contain both chemically reacted and chemically unreacted phosphonate monomers or phosphonate oligomers.

In certain embodiments, oligomeric polyesters can be combined with phosphonate oligomeric phosphonates and transesterification or condensation of these oligomeric components can be carried out to produce the polyester co-polyphosphonates. In such embodiments, the oligomeric polyesters may have reactive end groups such as but not limited to, acid, ester, hydroxyl, or carbonate, and the oligomeric phosphonates may include ester (phosphonate), acid (phosphonic acid), and/or hydroxyl end groups (i.e., hydroxyl termini). Any oligomeric phosphonate or oligomeric co-phosphonate known in the art can be used in the synthesis of the polyester co-polyphosphonates of the invention. For example, any of the oligomeric phosphonates having the structure properties described above can be used in the synthesis of the polyester co-polyphosphonates of embodiments. In certain embodiments, oligomeric phosphonates and oligomeric co-phosphonates may be those having the structures described in U.S. Pat. Nos. 6,861,499, 7,645,850, 7,816,486, and 8,389,664 each of which are hereby incorporated by reference in their entireties. In various embodiments, the oligomeric phosphonate may be derived from diaryl alkylphosphonates, diaryl arylphosphonates, or combinations thereof and an aromatic dihydroxy compound such as dihydric phenols, bisphenols, or combinations thereof. Such oligomeric phosphonates may be linear, branched, hyperbranched, or a combination thereof. Such oligomeric phosphonates and co-phosphonates may include ester (phosphonate), acid (phosphonic acid), and/or hydroxyl end groups (i.e., hydroxyl termini) and can be incorporated directly into the polyester during transesterification or polycondensation reactions described.

In some embodiments, about 60% to 100% of the total of the oligomeric phosphonates have two or more reactive end-groups, and in other embodiments, about 75% to about 99% of the total of oligomeric phosphonates have two or more reactive end-groups. In some embodiments, the reactive end-groups may be acid, ester, hydroxyl, or carbonate, and in certain embodiments, about 80% to about 100% of the total oligomeric phosphonates may have two or more acid, ester, hydroxyl, or carbonate or any combination of two of these end groups. In certain embodiments, the oligomeric phosphonate may have ester, a carbonate, or a combination of ester and carbonate end groups.

The oligomeric phosphonates may include linear oligomeric phosphonates, branched oligomeric phosphonates, hyperbranched oligophosphonates, or a combination thereof. These oligomeric phosphonates may have a number averaged molecular weight of from about 500 g/mole to about 5000 g/mole measured against PS standards, or in some embodiments, the oligomeric phosphonates may have a number averaged molecular weight of from about 1500 g/mole to about 3000 g/mole. In certain embodiments, the number averaged molecular weight of the oligomeric phosphonates can range from about 1,000 g/mole to about 10,000 g/mole, and in some embodiments, the number averaged molecular weight can range from about 2,000 g/mole to about 6,000 g/mole measured against PS standards.

The polyester portion of the polyester co-polyphosphonates prepared by the methods of the embodiments described above may have any molecular weight, and in certain embodiments may be from about 10,000 g/mol to about 50,000 g/mol, or about 20,000 g/mol to about 35,000 g/mol or any individual molecular weight or range encompassed by these ranges.

In some embodiments, polyester co-phosphonates prepared by the methods of the invention may include monomers that, when polymerized, are intended to provide aliphatic or aromatic thermoplastic polyesters including but not limited to poly(butylene terephthalate) (PBT), poly(ethylene terephtalate) (PET), Polyethylene Terephtalate Glycol-modified (PETG), poly(trimethylene terephthalate) (PTT), and polyalkylene naphthalates, such as, for example, polyethylene naphthalate, poly(trimethylene naphthalate), polybutylene naphthalate, polycaprolactone, poly(butylene adipate), poly(ethylene adipate), poly(hexamethylene sebacate), polylactic acid, polyglycolide and liquid crystalline polyesters such as those prepared from 4-hydroxybenzoic acid and 6-hydroxynaphthalene-2-carboxylic acid, glycolic acid and the like.

The methods described herein result in saturated and unsaturated polyesters that have phosphonates incorporated into the main chain, i.e., polyester co-phosphonates. The polyester co-phosphonates produced by these methods and described above are thermoplastic polyesters that exhibit acceptable melt processing characteristics as compared to the unmodified polyester, are spinnable into fibers and generally meet UL or similar standardized fire resistance ratings required for a variety of consumer products without detracting from other important safety, environmental, manufacturing and consumer use requirements.

The methods described above also overcome certain problems associated with melt mixing and extruding an oligomeric ester or polyester with low melting flame retardants such as, oligomeric phosphonates and polyphosphonates including different drying temperatures acceptable for the respective materials. For example, the polyester requires drying at temperatures of 120° C. or higher whereas the oligomeric phosphonates or polyphosphonates can only be dried at about 80° C. as higher temperatures can cause softening, sintering, or melting. Upon mixing the two, the higher temperature of the polyester causes the oligomeric phosphonate to begin to soften, sinter, and melt resulting in agglomeration that causes the extruder to clog, thereby halting the process. This is a significant problem in the production of flame retardant polyesters. The method leading to the compositions disclosed herein overcomes this problem as the phosphonate groups are chemically incorporated into the polyester. These polyester cophosphonates have high melting temperatures comparable to regular PET and consequently will not sinter or agglomerate during the feeding stage or the initial mixing stage of the melt extrusion process. Alternatively, the polyester co-phosphonates of the present invention can be used directly to spin fibers as a standalone material and have enough phosphor content to flame retard the fibers and resulting textiles.

Another advantage of the compositions described above is that the phosphorous content can be varied depending on the amount of phosphonate monomer or oligomeric phosphonate incorporated into the polyester. Commercial materials such as Trivera® CS and Toyobo HEIM® come already pre-formulated with a specific polyester chemistry with the phosphorus incorporated as phosphinic and phosphaphenanthrene derivatives, respectively. For these two products, it may not be possible to achieve the requisite phosphorus content necessary to meet flame resistance specifications if the molar mass of the monomers is large. Thus these two commercial materials lack the versatility that the polyester co-phosphonates and methods for producing these polyester co-phosphonates provide.

In further embodiments, methods may include the step of incorporating additional additives into the polyester co-phosphonates produced. For example, in some embodiments, additional additives can be incorporated after transesterification to improve one or more properties exhibited by the fiber or flame retardant polyester co-phosphonate. Non-limiting examples of such additional additives include fire resistant additives, fillers, dyes, antioxidants, pigments, anti-dripping agents, wetting agents, lubricating agents, and other additives typically used with polyesters. In some embodiments, the additives may be different depending on the intended use, for example, a fiber may have a different combination of additives as compared to a film. In particular embodiments, the polyester fibers or flame retardant polyesters may include a dye and/or pigment. In some embodiments, additional fire resistant additives may be included such as, but are not limited to, metal hydroxides, nitrogen containing flame retardants such as melamine cyanurate, phosphinate salts, organic phosphates, other phosphonates, organic sulfonate salts, perfluorinated sulfonate salts, siloxanes, and the like. In some embodiments, the polymer compositions may further include, for example, fillers such as talc, silica, clays, chopped or continuous glass fiber, metal fibers, organic fibers, aramid fibers, carbon fibers, carbon nanofibers, ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon black, graphite, graphene, graphene oxide, carbon nanotubes, carbon buckyballs, organic antistatics, polyalkylene ethers, alkylsulfonates, perfluoro sulfonic acid, perfluorbutane sulfonic acid potassium salt, polyamide-containing polymers, catalysts, colorants, inks, dyes, antioxidants, stabilizers, metal phosphinates, melamine cyanurate, melamine derivatives, flame retardants, or combinations thereof.

Such additives may be incorporated using any known method. For example, in some embodiments, the method of the invention may include the steps of compounding the one or more additional additives into the polyester co-phosphonates prepared as above. In other embodiments, one or more additives can be included in the polyester co-phosphonates prepared by the method of the invention by incorporating the additive into the initial reaction mixture or the reaction mixture during transesterification. The type of additive incorporated into the polyester co-phosphonates prepared as described above may dictate the means by which the additive is incorporated. The skilled artisan can determine the best method for incorporating each additive.

Other embodiments are directed to polyester co-phosphonate compositions including at least one polyester co-phosphonate and at least one polymer or second oligomer or monomer. Such compositions including an oligomeric phosphonate and a polymer or second oligomer or monomer are referred to herein as "polymer compositions." The at least one polymer or second oligomer or monomer may be any commodity or engineering plastic, and such polymer compositions can be produced by blending, mixing, or compounding the constituent polymers and oligomers. "Engineering plastics" as used herein include, both thermoplastics and thermosetting resins and may include, but are not limited to, polycarbonates, epoxies derived polymers, polyepoxies (e.g., polymers resulting from the reaction of one or more epoxy monomer or oligomer with one or more chain extender or curing agent such as a mono or multifunctional phenol, amine, benzoxazine, anhydride or combination thereof), benzoxazines, polyacrylates, polyacrylonitriles, polyesters, such as, poly(ethylene terephthalate), poly(trimethylene terephthalate), and poly(butylene terephthalate)], unsaturated polyesters, polyamides, polystyrenes including high impact strength polystyrene, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, or any combination thereof. The polymer or second oligomer may, therefore, include, or partially include one or more polycarbonate, polyacrylate, polyacrylonitrile, polyester, polyamide, polystyrene, polyurethane, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, polyether, polyphenylene oxide, cellulose polymer, benzoxazine, a hydrolytically stable polyphosphonate, and the like and combinations of these. In some embodiments, the polymer or second oligomer or monomer may contain functional groups that are capable of chemically reacting with the end groups of the polyester co-phosphonates of embodiments, and in certain embodiments in which the polyester co-phosphonates may include predominately hydroxyl or epoxy or vinyl termini, the polymer or second oligomer may contain functional groups capable of reacting with hydroxyl or epoxy or vinyl end groups.

The methods of some embodiments may further include the step of spinning the polyester co-phosphonates prepared as described above into fibers. The spinning process may vary in embodiment and may include melt spinning, gel spinning, solution spinning, or other known spinning techniques. In some embodiments, spinning may be carried out directly following preparation of the polyester co-phosphonate. Thus, the method may include for example, reacting the reaction mixture followed by, for example, melt-spinning, or compounding the polyester co-phosphonate with one or more additives followed by, for example, melt-spinning. In other embodiments, the polyester co-phosphonates produced by the methods of the invention may be pelletized and stored for a period of time. The pelletized polyester co-phosphonates may then be melted and spun into fibers using one of the spinning techniques identified above.

In particular embodiments in which the polyester co-phosphonates of the invention can be spun into fibers, the solution viscosity of the material may be modified to improve the processability of material during fiber spinning. In particular, the solution viscosities of the polyester co-phosphonates during fiber spinning may be from about 0.04 dL/g to about 3.0 dL/g, about 0.1 dL/g to about 2.5 dL/g, or about 0.5 dL/g to about 2.0 dL/g, or any value between these ranges. In some embodiments, the solution viscosities may depend on the end application. For example, textile grade fibers may be prepared from a polyester co-phosphonates having a solution viscosity of from about 0.04 dL/g to about 0.70 dL/g, and fibers for industrial applications such as tire cord may have a solution viscosity of from about 0.7 dL/g to about 1.0 dL/g. Monofilament fibers may be prepared from a polymer composition having a solution viscosity of from about 1.0 dL/g to about 2.0 dL/g.

In certain embodiments, methods for the preparation of polymer fibers may include the step of heat setting the spun fibers. The term "heat setting" as used herein refers to thermal processing of the fibers in either a steam atmosphere or a dry heat environment. Heat setting gives fibers, yarns, or fabric dimensional stability and can provide other desirable properties such as higher volume, wrinkle resistance, and/or temperature resistance.

In still other embodiments, the methods may include compressing the melt mixed material in rollers to create a film, spin casting a film, or blow molding the polyester co-phosphonate into a film.

The fibers of this invention can be used in woven and non-woven products. For example, the polymer compositions of various embodiments may be used in woven products such as clothing, carpet, flooring materials, wigs, and non-woven articles used in consumer products that must meet fire resistance standards. More particular, exemplary embodiments include fabrics that are woven or knitted from polyester fiber, thread or yarn that are used in apparel and home furnishings, such as shirts, pants, jackets, hats, bed sheets, blankets, upholstered furniture, packaging and the like. Non-woven fibers prepared from the polymer compositions of the invention can be used in other applications such as cushioning and insulating material in pillows, blankets, quilts, comforters, and upholstery padding, sheet material such as that used to wrap and insulate walls, and roofs in the construction of buildings, packaging and the like. Other embodiments include industrial polyester fibers, yarns, and ropes that are used, for example, in tire reinforcements, fabrics for conveyor belts, safety belts, coated fabrics, and plastic reinforcements with high-energy absorption and packaging.

The fibers of various embodiments may have any thickness or diameter, and the diameter of fibers may vary by their intended use. For example, in embodiments in which the fibers are used in textiles for clothing, the fiber diameter may be less than fibers used for carpeting or upholstery, which may have a smaller diameter than fibers used for industrial yarns and ropes. In some embodiments, the fiber diameter may be from about 2.0 µm to about 250 µm, about 5 µm to about 100 µm, about 10 µm to about 50 µm, or from about 12 µm to about 25 µm. In other embodiments, the density of the fiber may be from about 0.9 denier to about 2500 denier, about 2 denier to about 2000 denier, or 10 denier to about 1500 denier or any range between these ranges. A "denier" is a well-known unit of linear density in the textile arts and is defined herein as the weight in grams of 9000 meters of a linear material. The diameter of the fibers may also have any geometric shape, for example, round, oblong, corrugated patterns, random roughness, or other shapes that enhance their use in a specific application.

Some embodiments of the invention are directed to other articles of manufacture incorporating polymer compositions prepared as described above. For example, certain embodiments are directed to articles of manufacture such as, but not limited to, molded articles, "plastic" bottles, films and extruded sheets, tarpaulin, canoes, liquid crystal displays, holograms, filters, dielectric films, insulation for wires, insulating tapes, packaging materials, protective materials, and other films, moldings, and other articles including the polymer compositions. In other embodiments, fibers including the polymer compositions of the invention can be incorporated into fiber reinforced composites that include a matrix material that is compatible with the polymer compositions described above. Such fiber reinforced composites may be incorporated into any of the articles described above. In still other embodiments, the polymer compositions described herein may be incorporated into wood finishes that can be applied to wood products as a liquid or gel.

The methods of various embodiments are compatible with those commonly used by skilled artisans and may be carried out in, for example, stirred tanks, melt reactors, thin-film evaporators, falling-film evaporators, stirred tank cascades, extruders, kneaders, simple disc reactors, disc reactors for high viscosity substances, and combinations thereof. The devices, apparatuses and reactors suitable for the individual reaction evaporator stages may depend on the course of the process and may include, but are not limited to, heat exchangers, flash apparatuses, separators, columns, evaporators, stirred containers, reactors, and any other commercially available apparatuses which provide the necessary residence time at selected temperatures and pressures. The chosen devices must permit the necessary heat input and must be designed so that they are suitable for the continuously increasing melt viscosity. The various devices may be connected to one another via pumps, pipelines, valves, and the like, and combinations thereof. The pipelines between all facilities are preferably as short as possible and the number of bends in the pipes kept as small as possible in order to avoid unnecessarily prolonging residence times. The subsequent conversion of the polyester composition into a specific material form such as a film or a fiber can be conducted by a variety of techniques utilizing manufacturing equipment designed for this purpose. This may involve melt processing, solution processing or a combination of both.

The polymer compositions, polymer fibers, articles of manufacture, and such described herein exhibit excellent flame resistance and a superior combination of properties including processing characteristics, mechanical properties, heat-setting characteristics, and ability to dye as compared to fiber compositions containing conventional brominated or phosphorus-containing flame retardants. Because the phosphonate moieties are chemically bonded to within the polyester cophosphonates, they do not leach out and will generally not produce environmental concerns. Therefore, polymer compositions described herein including a thermoplastic polyester co-phosphonate meet all of the processing and performance requirements specified for polyesters forms including films and fibers, and also overcome the environmental and toxicity considerations. Moreover, formulations containing these flame retardant materials were spun into high quality fibers, woven into test articles and tested for flame resistant properties.

In some embodiments, the phosphonates of the invention may be combined with a prepolymer mixture composed of components selected to create a polyester such as those described above under conditions appropriate for polymerization. For example, in various embodiments, a phosphonate monomer or an oligomeric phosphonate such as those described above may be combined with a prepolymer mixture including one or more monomers for creating a polyester, and this mixture may be heated and mixed until a viscous polymer is formed, or in other embodiments, a polymerization catalyst may be provided to the mixture and mixing may continue until a high molecular weight polymer is formed.

In some embodiments the polymer compositions described here may further include additional components fillers, fibers, such as, but not limited to, chopped or continuous glass fiber, metal fibers, aramid fibers, carbon fibers, ceramic fibers, surfactants, organic binders, polymeric binders, crosslinking agents, diluents, coupling agents, flame retardant agents, anti-dripping agents such as fluorinated polyolefins, silicones, and lubricants, mould release agents such as pentaerythritol tetrastearate, nucleating agents, antistatic agents such as conductive blacks, carbon black, graphite, graphene, graphene oxide, carbon nanotubes, carbon buckyballs and organic antistatics such as polyalkylene ethers, alkylsulfonates, perfluoro sulfonic acid, perfluorbutane sulfonic acid potassium salt, and polyamide-containing polymers, catalysts, colorants, inks, dyes, antioxidants, stabilizers, and the like and any combinations thereof. In such embodiments, the one or more additional components or additives may make up from about 0.001 wt. % to about 1 wt. %, about 0.005 wt. % to about 0.9 wt. %, about 0.005 wt. % to about 0.8 wt. %, about 0.04 wt. % to about 0.8 wt. %, and in particular embodiments, from about 0.04 wt. % to about 0.6 wt. % based on the total composition. Certain additives such as, for example, flame retardant additives, phosphonates, melamine, melamine salts, and melamine cyanurate, and aluminum trihydrate, may be provided at higher concentrations such as, for example, from about 1 wt. % to about 30 wt. %, about 5 wt. % to about 25 wt. %, or about 10 wt. % to about 20 wt. % or any range between these exemplary ranges. In other embodiments, additional components such as glass fiber or other fillers may be provided at much higher concentrations up to 70 volume (vol.) %. For example, in some embodiments, the polyester co-phosphonate compositions may include up to about 70 vol. % glass fiber, and in other embodiments, the polymer compositions may include from about 5 vol. % to about 70 vol. %, from about 10 vol. % to about 60 vol. %, or about 20 vol. % to about 50 vol. % glass fiber.

Polymer compositions including phosphonates and polyesters or precursor monomers and/or additional components or additives can be prepared by conventional means in any sequence. For example, in some embodiments, the respective constituents can be mixed in a known manner and subjected to melt compounding and/or melt extrusion at temperatures of about 200° C. to about 400° C. in customary aggregates such as internal kneaders, extruders, or twin-screw apparatuses. Likewise, they can be subjected to melt spinning processes to produce monofilament or multifilament fibers. Mixing the individual constituents can be affected either successively or simultaneously and either at about room temperature (about 20° C.) or at higher temperature. For example, in some embodiments, the polyester and/or all additional components or additives can be introduced into the polyester co-phosphonates by compounding. In other embodiments, the individual constituents can be introduced separately in different stages of the preparation process into a melt including phosphonates. Thus, for example, additives can be introduced during or at the end of the mixing, before or during the formation of the polyester or before or after the mixing of the phosphonates into a melt.

The form of addition of the compounds according to the invention is not limited. For example, the oligomeric phosphonate, polyester and/or additional components or additives can be added as solids such as a powder, as concentrate in solution or a slurry in a liquid. In industrial embodiments, a side extruder may be operated with a throughput of, for example, 200-1000 kg of oligomeric phosphonate per hour.

The polyester co-phosphonate compositions are generally self-extinguishing, they stop burning when removed from a flame and any drops produced by melting in a flame stop burning, almost instantly extinguishes and do not readily propagate fire to any surrounding materials. Moreover, these polymer compositions do not evolve noticeable smoke when a flame is applied. They are particularly suited for the preparation of fibers.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Materials

A hydroxyl terminated phosphonate (Nofia® OL1001, manufactured by FRX Polymers®, Inc.) was titrated by acetic anhydride, resulted in acid number of 78 mg KOH/g. A number average molecular weight (Mn) of 840 g/mol and a weight average molecular weight (Mw) of 1,780 g/mol from the Nofia® OL1001 were obtained by the gel permeation chromatography based on a polystyrene calibration curve. A phenoxy terminated phosphonate (Nofia® OL3000, obtained from FRX Polymers®, Inc.) was titrated and resulted in acid number of 22 mg KOH/g. Mn was 1,800 g/mole and Mw was 5,700 g/mole. Diphenyl methyl phosphonate (DPP) was prepared by heating a mixture of triphenylphosphite and iodomethane to 240° C. and then slowly adding trimethylphosphite over 3.5 hrs. The reaction mixture was maintained at 240-260° C. until gas chromatography of reaction sample aliquots did not show the presence of any of the starting materials anymore.

Dimethyl terephthalate, terephthalic acid, adipic acid, antimony trioxide and zinc acetate from Sigma-Aldrich were used as received. Ethylene glycol was purchased from VWR International and used without further purification.

Methods

HPLC: All compounds in distillate were determined by High Performance Liquid Chromatography (HPLC). The mobile phase was acetonitrile.

DSC: Glass transition temperatures (Tg) were measured using differential scanning calorimetry (DSC). The material was heated at a rate of 10° C./min to 260° C. After keeping the sample at this temperature for 10 minutes, the temperature of the sample was decreased at a rate of 10° C./min to −30° C. The Tg was determined during a second heating cycle (10° C./min to 350° C.) based on the ½ Cp method.

ICP-OES: The % phosphorus was determined using inductively coupled plasma optical emission spectrometry (ICP-OES).

Comparative Example 1

Synthesis of Polyethylene Terephthalate

A 500 mL, three-necked round bottom flask equipped with a mechanical stirrer, distillation column filled with hollow glass condenser, and vacuum adapter with control valve was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2 \cdot 2H_2O$, 0.14 mmoles) were placed into the flask and the reactor was placed in an oil bath and heated to 190° C. while stirring for 150 minutes. Theoretical amount of methanol was generated and collected via column. 0.03 g of antimony trioxide ($Sb_2O_3$, 0.22 mmoles) was added to the reactor and heated up to 280° C. while stirring for 240 minutes. Pressure was gradually lowered to 4 mmHg over 180 minutes, and maintained full vacuum (0.3 mmHg) for 60 more minutes. The distillate was collected in a flask cooled in an ice bath. The product was isolated as a white solid (102 g). DSC Tg was 79° C. and Tm was 256° C.

Example 1

Synthesis of Poly(ethylene terephthalate-co-methyl phosphonate)

A 500 mL, three-necked round bottom flask equipped as same as in Comparative Example 1 was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2 \cdot 2H_2O$, 0.14 mmoles) were placed into the flask and the reactor was placed in an oil bath and heated to 190° C. while stirring for 150 minutes. 25.6 g of methanol was generated and collected via column. 99.28 g of diphenyl methyl phosphonate (0.4 moles) and 2.6 mg of sodium hydroxide (NaOH, 0.065 mmoles) in 2.6 mL of water were added to the reactor and maintained 265° C. while stirring. Pressure was gradually lowered to 4 mmHg over 240 minutes and temperature of the oil bath was gradually increased up to 300° C. during last 60 minutes. The distillate was collected in a flask cooled in an ice bath. In an attempt to build up to high molecular weight and to remove unreacted diphenyl methyl phosphonate, full vacuum (0.3 mmHg) was applied for 150 more minutes. The viscosity of the reaction mixture substantially increased. At the end of the reaction a highly viscous mass was produced and upon cooling, the final product was isolated as a light yellow solid (150 g). Analytical % P was 4.0 wt. %. DSC Tg was 43° C. and Tm was 202° C. HPLC analysis of the distillate indicated the presence of 0.48 mole of phenol, 0.575 mole of ethylene glycol and small trace of diphenyl methyl phosphonate.

Example 2

Synthesis of Poly(ethylene terephthalate-co-methyl phosphonate)

A 500 mL, three-necked round bottom flask equipped as same as in Comparative Example 1 was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2 \cdot 2H_2O$, 0.14 mmoles) were placed into the flask and the reactor was placed in an oil bath and heated to 190° C. while stirring for 150 minutes. 25.6 g of methanol was generated and collected via column. 99.28 g of diphenyl methyl phosphonate (0.4 moles) and 2.6 mg of sodium hydroxide (NaOH, 0.065 mmoles) in 2.6 mL of water were added to the reactor and maintained 265° C. while stirring. Pressure was gradually lowered to 4 mmHg over 240 minutes, and temperature of the oil bath was gradually increased up to 280° C. during last 60 minutes. The distillate was collected in a flask cooled in an ice bath. In an attempt to build up to high molecular weight and to remove unreacted diphenyl methyl phosphonate, full vacuum (0.3 mmHg) was applied for 150 more minutes. The viscosity of the reaction mixture substantially increased. At the end of the reaction a highly viscous mass was produced and upon cooling, the final product was isolated as a light yellow solid (135 g). Analytical % P was 5.0 wt. %. DSC Tg was 17° C. and Tm was 192° C. HPLC analysis of the distillate indicated the presence of 0.59 mole of phenol, 0.53 mole of ethylene glycol and small trace of diphenyl methyl phosphonate.

Example 3

Synthesis of Poly(ethylene terephthalate-co-methyl phosphonate)

A 500 mL, three-necked round bottom flask equipped as same as in Comparative Example 1 was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2 \cdot 2H_2O$, 0.14 mmoles) were placed into the flask and the reactor was placed in an oil bath and heated to 190° C. while stirring for 150 minutes. 25.6 g of methanol was generated and collected via column. 4.96 g of diphenyl methyl phosphonate (0.02 moles) and 2.6 mg of sodium hydroxide (NaOH, 0.065 mmoles) in 2.6 mL of water were added to the reactor and maintained 265° C. while stirring. Pressure was gradually lowered to 4 mmHg over 360 minutes, and the distillate was collected in a flask cooled in an ice bath. In an attempt to build up to high molecular weight and to remove unreacted diphenyl methyl phosphonate, full vacuum (0.3 mmHg) was applied for 150 more minutes. The distillate was collected in a flask cooled in an ice bath. The viscosity of the reaction mixture substantially increased. At the end of the reaction a highly viscous mass was produced and upon cooling, the final product was isolated as a white solid (85 g). Analytical % P was 0.1 wt. %. DSC Tg was 77° C. and Tm was 251° C. HPLC analysis of the distillate indicated the presence of 0.003 mole of phenol and 0.57 mole of ethylene glycol.

Example 4

Synthesis of Poly(ethylene terephthalate-co-oligomeric phosphonate)

A 500 mL, three-necked round bottom flask equipped as same as in Comparative Example 1 was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2.2H_2O$, 0.14 mmoles) were placed into the flask and the reactor was placed in an oil bath and heated to 190° C. while stirring for 150 minutes. Methanol was generated and collected via column. 0.03 g of antimony trioxide $(Sb_2O_3$, 0.22 mmoles) was added to the reactor and increased temperature up to 280° C. and pressure was lowered to 200 mmHg while stirring for 60 minutes. Remaining ethylene glycol was collected instantly and then ethylene glycol formed from self condensation started to distill off slowly. Pressure was released and 14.4 g of Nofia® OL1001 (0.01 moles) was added to the reactor. Pressure was gradually lowered to 4 mmHg over 150 minutes maintaining 280° C. The distillate was collected in a flask cooled in an ice bath. The viscosity of the reaction mixture substantially increased. At the end of the reaction a highly viscous mass was produced and upon cooling, the final product was isolated as a light yellow solid (115 g). Analytical % P was 0.8 wt. %. DSC Tg was 54° C. and Tm was 230° C. HPLC analysis indicated that distillate was the ethylene glycol.

Example 5

Synthesis of Poly(ethylene terephthalate-co-oligomeric phosphonate)

A 500 mL, three-necked round bottom flask equipped as same as in Comparative Example 1 was flushed with nitrogen for a 0.5 hour. 77.67 g of dimethyl terephthalate (0.4 moles) and 59.59 g of ethylene glycol (0.96 moles), and 0.03 g of zinc acetate hydrate $(Zn(O_2CCH_3)_2.2H_2O$, 0.14 mmoles) were placed into the flask and the reactor was placed in an oil bath and heated to 190° C. while stirring for 150 minutes. Theoretical amount of methanol was generated and collected via column. 14 g of Nofia® OL3000 (0.005 moles) and 0.03 g of antimony trioxide $(Sb_2O_3$, 0.22 mmoles) were added to the reactor and maintained 280° C. while stirring. Pressure was gradually lowered to 4 mmHg over 300 minutes, and maintained full vacuum (0.3 mmHg) for 120 more minutes. The distillate was collected in a flask cooled in an ice bath. The viscosity of the reaction mixture substantially increased. At the end of the reaction a highly viscous mass was produced and upon cooling, the final product was isolated as a light yellow solid (102 g). Analytical % P was 0.2 wt. %. DSC Tg was 64° C. and Tm was 206° C. HPLC analysis indicated that distillate was the ethylene glycol.

Example 6

To check the change in crystallinity of the Examples 1-5 compared to PET Comparative Example 1, heat of fusion data obtained from DSC were utilized and displayed in Table 1 below.

TABLE 1

Crystallinity of Comparative Example 1 and Examples 1-5

| Sample | Tm (° C.) | Heat of fusion (J/g) | Crystallinity (%) |
| --- | --- | --- | --- |
| Comparative Example 1 | 256 | 55 | 60 |
| Example 1 | 202 | 32 | 35 |
| Example 2 | 192 | 27 | 29 |
| Example 3 | 251 | 40 | 44 |
| Example 4 | 230 | 41 | 46 |
| Example 5 | 206 | 28 | 31 |

Example 7

DSC Measurement of PET, PBT, and /Nofia® HM1100 Blends

To verify that the samples in Examples 1-5 are actual polyester co-phosphonates and not physical blends of a polyester and a polyphosphonate, Tg and Tm of PET (or PBT) blends with Nofia® HM1100 were obtained by running DSC. The result is displayed in Table 2.

TABLE 2

DSC result of PET, PBT, and NOFIA® HM1100 blends.

| Sample | % P (wt. %) | Tg (° C.) | Tm (° C.) |
| --- | --- | --- | --- |
| PET + 5 wt. % Nofia ® HM1100 | 0.5 | 71, 103 | 248 |
| PET/PBT + 12.5 wt. % Nofia ® HM1100 | 1.3 | 49, 85, 95 | 217, 248 |
| PBT + 50 wt % Nofia ® HM1100 | 5.0 | 45, 96 | 224 |

All of the samples from Table 2 show the two or three glass transition temperatures of the individual components in the blends instead of a single Tg like was reported for the examples 1-5.

Example 8

Flame Retardancy Test

The synthesized products in Comparative Example 1 and Examples 1-5 were shaped with a compression molding to form test specimen with 0.8 mm thickness. A specimen vertically clamped at its upper end was burned by application of standard flame to its lower end for 10 seconds. The time required for the test specimen to burn until the fire goes out was measured (the first flame times, T1). Immediately after that, the test specimen was burned again by the application of a standard flame for 10 seconds. The time required for the test specimen to burn until the fire goes out was measured (the second flame times, T2). The measurement was repeated for four test specimens. The results of all specimens are shown in Table 3.

TABLE 3

Flame retardancy of Comparative Example 1 and Examples 1-5

| Sample | % P (wt. %) | T1 + T2 (sec.) | | UL94 rating |
|---|---|---|---|---|
| Comparative Example 1 | 0 | 90 | flaming drip | V2 |
| Example 1 | 4.0 | 0 | | V0 |
| Example 2 | 5.0 | 0 | | V0 |
| Example 3 | 0.1 | 28 | flaming drip | V2 |
| Example 4 | 0.8 | 0 | | V0 |
| Example 5 | 0.2 | 17 | flaming drip | V2 |

The results from Table 3 confirm the flame retardancy of the polyester co-phosphonates at sufficient high % P when molded in 0.8 mm bars. To obtain a UL94 V0 rating at a different thickness, a different minimum % P may be required. Also, other FR tests or using articles in a different shape than a molded bar may require a different % P level and the composition will be needed to optimized for each separate application.

Example 9

Sintering Test

Sintering behavior of plastic pellets affects the temperature for drying. When plastic materials are dried at too high of a temperature, the pellets may start to agglomerate (sinter). This is unwanted as these agglomerates may block the feeding lines to the extruder or block the feed throat of the extruder. Sintering behavior of materials was tested by filling pellet samples in a glass jar, and then placing the jar in the middle of a vacuum oven. Heating was started at 80° C., which is recommended drying temperature for polyphosphonate Nofia® HM1100, and temperatures were increase to 125° C., 135° C., 145° C. and 155° C. After two hours at each temperature, the jar was opened and turned upside down. Sintering behavior was checked by observing how much pellets would freely drop out from the bottom of the jar. When NOFIA HM1100 is subjected to this test, the material will start to agglomerate (sinter) at 95° C. The results of the examples are displayed in Table 4.

TABLE 4

Sintering behavior of Comparative Example 1 and Examples 1-5

| Sample | % P (wt. %) | Tm (° C.) | 95° C. | 135° C. 2 hrs. | 145° C. 2 hrs. | 155° C. 2 hrs. |
|---|---|---|---|---|---|---|
| Comparative Example 1 | 0 | 256 | o | o | o | o |
| Example 1 | 4.0 | 202 | o | o | sintering | |
| Example 2 | 5.0 | 192 | sintering | | | |
| Example 3 | 0.1 | 251 | o | o | o | o |
| Example 4 | 0.8 | 230 | o | o | o | o |
| Example 5 | 0.2 | 206 | o | sintering | | |

These data indicated that it is possible to prepare polyester co-phosphonates that show a sintering temperature that is much higher than NOFIA HM1100 and therefore can be dried at temperatures that are also used to dry regular PET. This will overcome the issues to add two streams of pellets together (a hot PET and a colder polyphosphonate-ester) with the risk that the temperature of the colder pellets increase and will induce sintering of these pellets. It even may be possible to dry the polyester co-phosphonates of the present invention together with regular PET in the same drying equipment.

The invention claimed is:
1. A method for preparing a polyester co-phosphonate comprising:
   combining at least one diol, at least one dicarboxylic acid or at least one di-ester, and at least one oligomeric phosphonate of Formula II:

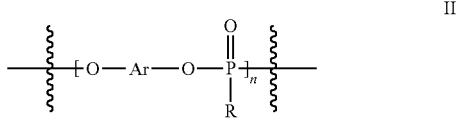

wherein:
   —O—Ar—O— is derived from bisphenol A, bisphenol F, 4,4'-biphenol, phenolphthalein, 4,4'-thiodiphenol, 4,4'-sulfonyldiphenol, 3,3,5-trimethylcyclohexyldiphenol, or combinations thereof;
   R is a $C_{1-20}$ alkyl, $C_{2-20}$ alkenyl, $C_{2-20}$ alkynyl, $C_{5-20}$ cycloalkyl, or $C_{6-20}$ aryl; and
   n is an integer from 2 to about 10,
   to form a reaction mixture; and
   reacting the reaction mixture;
   wherein the phosphonate is incorporated into a polyester to form the polyester co-phosphonate.
2. The method of claim 1, wherein the method is carried out in a batch process or a continuous process.
3. The method of claim 1, further comprising adding at least one AB monomer into the reaction mixture.
4. The method of claim 1, further comprising introducing a catalyst into the reaction mixture.
5. The method of claim 1, wherein the oligomeric phosphonate comprises about 1 wt. % to about 80 wt. % of the reaction mixture.
6. The method of claim 1, wherein the diol is selected from the group consisting of 1,4-cyclohexyldimethanol, 1,4-butane diol, 1,3-propane diol, ethylene diol, and combinations thereof.
7. The method of claim 1, wherein the diol is ethylene glycol.
8. The method of claim 1, wherein the diol is selected from the group consisting of 4,4'-dihydroxybiphenyl, hydroquinone, resorcinol, methyl hydroquinone, chlorohydroquinone, acetoxyhydroquinone, nitrohydroquinone, 1,4-dihydroxynaphthalene, 1,5-dihydroxynaphthalene, 1,6-dihydroxynaphthalene, 2,6-dihydroxynaphthalene, 2,7-dihydroxynaphthalene, 2,2-bis(4-hydroxyphenyl)propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl) propane, bis(4-hydroxyphenyl)methane, bis(4-hydroxy-3,5-dimethyl phenyl)methane, bis(4-hydroxy-3,5-dichlorophenyl)methane, bis(4-hydroxy-3,5-dibromophenyl)methane, bis(4-hydroxy-3-methylphenyl) methane, bis(4-hydroxy-3-chlorophenyl)methane, 1,1-bis (4-hydroxyphenyl)cyclohexane, bis(4-hydroxyphenyl) ketone, bis(4-hydroxy-3,5-dimethylphenyl)ketone, bis(4-hydroxy-3,5-dichlorophenyl)ketone, bis(4-hydroxyphenyl) sulfide, and bis(4-hydroxyphenyl) sulfone.
9. The method of claim 1, wherein the at least one dicarboxylic acid or at least one di-ester is selected from the group consisting of adipic acid, terephthalic acid, isophthalic acid, naphthalene dicarboxylic acid, and combinations thereof.

10. The method of claim 1, wherein the at least one dicarboxylic acid or at least one di-ester is selected from the group consisting of dimethyl terephthalate, dimethyl isophthalate, dimethyl naphthalate, and combinations thereof.

11. The method of claim 1, further comprising introducing one or more additives into the polyester co-phosphonate.

12. The method of claim 11, wherein introducing the one or more additives into the polyester co-phosphonate is carried out during or after reacting.

13. The method of claim 1, further comprising pelletizing the polyester co-phosphonate.

14. The method of claim 1, further comprising spinning the polyester co-phosphonate into fibers.

15. The method of claim 14, further comprising heat setting the fibers.

16. The method of claim 14, further comprising weaving the fibers into fabric or twisting the fibers into yarn.

17. The method of claim 1, further blending the polyester co-phosphonate and one or more engineering polymers.

18. The method of claim 17, wherein the one or more engineering polymer comprises a polyester.

19. The method of claim 17, further comprising spinning the blended polyester co-phosphonate and one or more engineering polymer into fibers.

* * * * *